(12) United States Patent
Ichinose

(10) Patent No.: US 12,288,611 B2
(45) Date of Patent: Apr. 29, 2025

(54) INFORMATION PROCESSING APPARATUS, METHOD, AND PROGRAM

(71) Applicant: FUJIFILM Corporation, Tokyo (JP)

(72) Inventor: Akimichi Ichinose, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 342 days.

(21) Appl. No.: 17/887,497

(22) Filed: Aug. 14, 2022

(65) Prior Publication Data

US 2022/0392619 A1 Dec. 8, 2022

Related U.S. Application Data

(63) Continuation of application No. PCT/JP2021/006422, filed on Feb. 19, 2021.

(30) Foreign Application Priority Data

Feb. 20, 2020 (JP) ................................ 2020-027210

(51) Int. Cl.
*G16H 30/40* (2018.01)
*G06T 7/00* (2017.01)
*G16H 15/00* (2018.01)

(52) U.S. Cl.
CPC ........... *G16H 30/40* (2018.01); *G06T 7/0016* (2013.01); *G16H 15/00* (2018.01); *G06T 2200/04* (2013.01); *G06T 2200/24* (2013.01); *G06T 2207/10072* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| | | | | |
|---|---|---|---|---|
| 7,751,603 | B2 * | 7/2010 | Yamasaki | A61B 5/0013 382/128 |
| 10,524,754 | B2 * | 1/2020 | Goshen | A61B 6/481 |
| 11,488,337 | B2 * | 11/2022 | Kunieda | H04N 23/951 |
| 2002/0057828 | A1 * | 5/2002 | Oosawa | G06T 7/60 382/132 |
| 2011/0066635 | A1 | 3/2011 | Moriya | |
| 2016/0314247 | A1 | 10/2016 | Nagao et al. | |

(Continued)

FOREIGN PATENT DOCUMENTS

| | | |
|---|---|---|
| JP | 2011062283 | 3/2011 |
| JP | 2016202722 | 12/2016 |

(Continued)

OTHER PUBLICATIONS

"Office Action of Japan Counterpart Application", issued on Oct. 3, 2023, with English translation thereof, p. 1-p. 8.

(Continued)

*Primary Examiner* — Michelle M Entezari Hausmann
(74) *Attorney, Agent, or Firm* — JCIPRNET

(57) ABSTRACT

An information processing apparatus includes at least one processor, and the processor derives a property for at least one predetermined property item which is related to a structure of interest included in an image. The processor specifies a basis region serving as a basis for deriving the property related to the structure of interest for each property item and derives a basis image including the basis region.

10 Claims, 18 Drawing Sheets

(56) References Cited

U.S. PATENT DOCUMENTS

| | | |
|---|---|---|
| 2018/0289336 A1 | 10/2018 | Osawa |
| 2019/0279751 A1 | 9/2019 | Nakamura et al. |
| 2019/0282344 A1* | 9/2019 | Azernikov ............ A61C 9/0053 |
| 2019/0287665 A1* | 9/2019 | Forsberg ................. G16H 50/30 |
| 2019/0388123 A1* | 12/2019 | Pavlovskaia ............ G06T 19/00 |
| 2020/0330063 A1* | 10/2020 | Thibault Pelletier ..... G06T 7/20 |
| 2020/0342990 A1 | 10/2020 | Ichinose et al. |

FOREIGN PATENT DOCUMENTS

| | | |
|---|---|---|
| JP | 2018175227 | 11/2018 |
| JP | 2019153250 | 9/2019 |
| WO | 2019146357 | 8/2019 |

OTHER PUBLICATIONS

Ramprasaath R. Selvaraju et al., "Grad-CAM: Visual Explanations from Deep Networks via Gradient-based Localization", Proceedings of the IEEE International Conference on Computer Vision, 2017, Dec. 2019, pp. 1-23.

Daniel Smilkov et al., "SmoothGrad: removing noise by adding noise", arXiv:1706.03825v1, Jun. 2017, pp. 1-10.

"International Search Report (Form PCT/ISA/210) of PCT/JP2021/006422", mailed on Apr. 20, 2021, with English translation thereof, pp. 1-5.

"Written Opinion of the International Searching Authority (Form PCT/ISA/237) of PCT/JP2021/006422", mailed on Apr. 20, 2021, with English translation thereof, pp. 1-7.

\* cited by examiner

INFORMATION PROCESSING APPARATUS, METHOD, AND PROGRAM

CROSS REFERENCE TO RELATED APPLICATIONS

The present application is a Continuation of PCT International Application No. PCT/JP2021/006422, filed on Feb. 19, 2021, which claims priority to Japanese Patent Application No. 2020-027210, filed on Feb. 20, 2020. Each application above is hereby expressly incorporated by reference, in its entirety, into the present application.

BACKGROUND

Technical Field

The present disclosure relates to an information processing apparatus, method, and program for supporting creation of interpretation reports and the like.

Related Art

In recent years, advances in imaging apparatuses, such as computed tomography (CT) apparatuses and magnetic resonance imaging (MRI) apparatuses, have enabled image diagnosis using high-resolution medical images with higher quality. In particular, since a region of a lesion can be accurately specified by image diagnosis using CT images, MM images, and the like, appropriate treatment is being performed based on the specified result.

In addition, image diagnosis is also made by analyzing a medical image via computer-aided diagnosis (CAD) using a learning model in which machine learning is performed by deep learning or the like, discriminating properties such as the shape, density, position, and size of structures of interest such as abnormal shadow candidates included in the medical images, and acquiring them as an analysis result. The analysis result acquired by CAD is associated with examination information such as a patient name, gender, age, and a modality that has acquired the medical image, and is saved in a database. The medical image and the analysis result are transmitted to a terminal of a radiologist who interprets the medical images. The radiologist interprets the medical image by referring to the transmitted medical image and analysis result and creates an interpretation report, in his or her own terminal.

In addition, a method of specifying a structure of interest included in an image using a learning model and deriving a region serving as a basis for specifying the structure in the image has been proposed (see Selvaraju, Ramprasaath R., et al. "Grad-cam: Visual explanations from deep networks via gradient-based localization." Proceedings of the IEEE International Conference on Computer Vision. 2017, hereinafter referred to as Non-Patent Document 1). The method described in Non-Patent Document 1 is a method in which, for example, in an image including a dog and a cat, a process of specifying each of the dog and the cat is performed using a learning model, a region serving as a basis for specifying the dog and the cat is specified, and the specified region is emphasized by, for example, a heat map or the like to display the image. This method is called Gradient-weighted Class Activation Mapping (Grad-CAM). Further, in the method described in Non-Patent Document 1, a method of specifying and displaying a region including pixels having a large prediction score, which serves as a basis for specifying the dog and the cat, by using an error backpropagation method has also been proposed. The region serving as a basis for specifying the dog is the region such as the drooping ears, eyes, and cheeks, and the region serving as a basis for specifying the cat is the region such as the striped pattern of the body. This method is called Guided Backpropagation. Via the method described in Non-Patent Document 1, it is possible to recognize the region serving as a basis for specifying the structure in the image. Further, in the method described in Non-Patent Document 1, a method of reducing the influence of noise included in an image by adding Gaussian noise to the image to perform smoothing has also been proposed (see Daniel Smilkov et al., "SmoothGrad: removing noise by adding noise", arXiv: 1706.03825, 12 Jun. 2017).

Meanwhile, with the improvement of the performance of the imaging apparatus, the number of medical images to be interpreted is also increasing. However, since the number of radiologists has not kept up with the number of medical images, it is desired to reduce the burden of the image interpretation work of the radiologists. Therefore, various methods have been proposed to support the creation of medical documents such as interpretation reports. For example, JP2019-153250A proposes various methods for generating a sentence to be included in an interpretation report based on keywords input by a radiologist and on information indicating a property of a structure of interest (hereinafter referred to as property information) included in an analysis result of a medical image. In the methods described in JP2019-153250A, a sentence relating to medical care (hereinafter referred to as a medical sentence) is created by using a learning model in which machine learning is performed to generate a sentence representing the input property information. By automatically generating the medical sentence as in the method described in JP2019-153250A, it is possible to reduce a burden on a radiologist at the time of creating a medical document such as an interpretation report.

A radiologist may interpret a plurality of tomographic images obtained by one imaging with an imaging apparatus such as a CT apparatus and an MM apparatus, and describe comments on findings for the property related to the structure of interest obtained from the respective tomographic images in an interpretation report. In this case, the interpretation report is created so that it can be seen in which tomographic image the findings described in the interpretation report can be recognized. Specifically, an interpretation report is created by pasting an image including a structure of interest with findings in the interpretation report or by adding a hyperlink to an image including a structure of interest with findings. However, creating an interpretation report by manually specifying an image including such a structure of interest by a radiologist is a burden on the interpretation work.

SUMMARY OF THE INVENTION

The present disclosure has been made in consideration of the above circumstances, and an object thereof is to support creation of medical documents such as interpretation reports.

According to an aspect of the present disclosure, there is provided an information processing apparatus comprising at least one processor, in which the processor is configured to derive property information indicating a property for at least one predetermined property item which is related to a structure of interest included in an image, and specify, in the image, a basis region serving as a basis for deriving the property related to the structure of interest for each property item and derive a basis image in which the basis region is specified.

In the information processing apparatus according to the aspect of the present disclosure, the processor may be configured to, in a case where the image is a three-dimensional image consisting of a plurality of tomographic images, select, for each property item, a tomographic image including the basis region that most prominently represents the property of the property item from among the plurality of tomographic images as the basis image to derive the basis image.

In the information processing apparatus according to the aspect of the present disclosure, the processor may be configured to, in a case where the image is a three-dimensional image consisting of a plurality of tomographic images, generate, for each property item, a basis image including the basis region that most prominently represents the property of the property item from the plurality of tomographic images to derive the basis image.

In the information processing apparatus according to the aspect of the present disclosure, the processor may be configured to derive the property for the property item in which a change has occurred with respect to the structure of interest between a first image acquired at a first point in time and a second image acquired at a second point in time different from the first point in time, and for the property item in which the change has occurred in the property between the first image and the second image, specify the basis region in at least one of the first image or the second image and derive the basis image.

In the information processing apparatus according to the aspect of the present disclosure, the processor may be configured to display a designation button for designating at least one property item on a display, and select the designation button to display a basis image for a property item corresponding to the selected designation button on the display.

In the information processing apparatus according to the aspect of the present disclosure, the processor may be configured to analyze a sentence including phrases related to the property item to specify a phrase related to the property item included in the sentence and add, to the specified phrase, information for accessing the basis image serving as a basis for deriving the property represented by the specified phrase, and display the sentence on a display and display the basis image corresponding to the phrase selected in the sentence on the display.

In the information processing apparatus according to the aspect of the present disclosure, the processor may be configured to generate the sentence by using the property for the property item.

In the information processing apparatus according to the aspect of the present disclosure, the processor may be configured to highlight the basis region in the displayed basis image.

According to another aspect of the present disclosure, there is provided an information processing method including: deriving property information indicating a property for at least one predetermined property item which is related to a structure of interest included in an image; and specifying, in the image, a basis region serving as a basis for deriving the property related to the structure of interest for each property item and deriving a basis image in which the basis region is specified.

In addition, the present disclosure includes a non-transitory computer-readable storage medium that stores an information processing program for causing a processor of an information processing apparatus to execute the aforementioned information processing method.

According to the aspects of the present disclosure, it is possible to support creation of a document such as an interpretation report.

DETAILED DESCRIPTION

Figure 1:
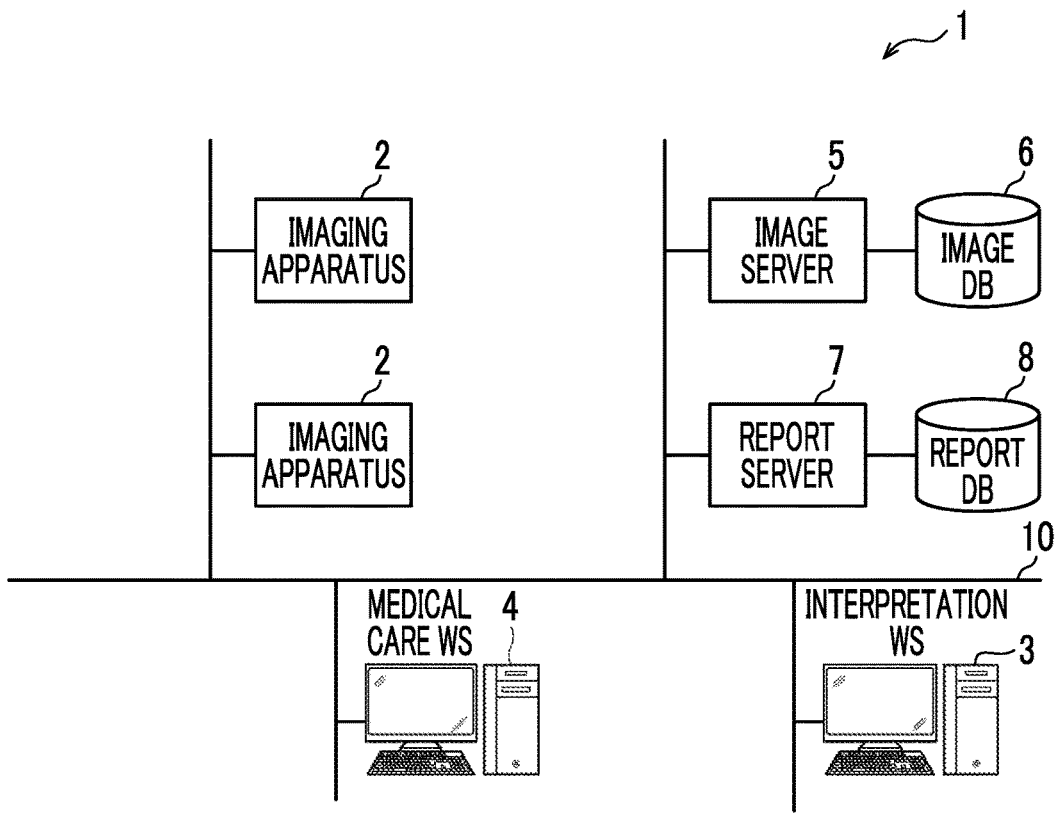
FIG. 1 is a diagram showing a schematic configuration of a medical information system to which an information processing apparatus according to a first embodiment of the present disclosure is applied.

Hereinafter, embodiments of the present disclosure will be described with reference to the drawings. First, a configuration of a medical information system 1 to which an information processing apparatus according to the present embodiment is applied will be described. FIG. 1 is a diagram showing a schematic configuration of the medical information system 1. The medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

As shown in FIG. 1, in the medical information system 1, a plurality of imaging apparatuses 2, a plurality of interpretation workstations (WSs) 3 that are interpretation terminals, a medical care WS 4, an image server 5, an image database (hereinafter referred to as an image DB) 6, a report server 7, and a report database (hereinafter referred to as a report DB) 8 are communicably connected to each other through a wired or wireless network 10.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed on the computer from the recording medium. Alternatively, the application program is stored in a storage apparatus of a server computer connected to the network 10 or in a network storage in a state in which it can be accessed from the outside, and is downloaded to and installed on the computer in response to a request.

The imaging apparatus 2 is an apparatus (modality) that generates a medical image showing a diagnosis target part of the subject by imaging the diagnosis target part. Specifically, examples of the modality include a simple X-ray imaging apparatus, a CT apparatus, an MRI apparatus, a positron emission tomography (PET) apparatus, and the like. The medical image generated by the imaging apparatus 2 is transmitted to the image server 5 and is saved in the image DB 6.

The interpretation WS 3 is a computer used by, for example, a radiologist of a radiology department to interpret a medical image and to create an interpretation report, and encompasses an information processing apparatus 20 (which will be described in detail later) according to the present embodiment. In the interpretation WS 3, a viewing request for a medical image to the image server 5, various image processing for the medical image received from the image server 5, display of the medical image, and input reception of comments on findings regarding the medical image are performed. In the interpretation WS 3, an analysis process for medical images and input comments on findings, support for creating an interpretation report based on the analysis result, a registration request and a viewing request for the interpretation report to the report server 7, and display of the interpretation report received from the report server 7 are performed. The above processes are performed by the interpretation WS 3 executing programs for respective processes.

The medical care WS 4 is a computer used by a doctor in a medical department to observe an image in detail, view an interpretation report, create an electronic medical record, and the like, and is configured to include a processing apparatus, a display apparatus such as a display, and an input apparatus such as a keyboard and a mouse. In the medical care WS 4, a viewing request for the image to the image server 5, display of the image received from the image server 5, a viewing request for the interpretation report to the report server 7, and display of the interpretation report received from the report server 7 are performed. The above processes are performed by the medical care WS 4 executing programs for respective processes.

The image server 5 is a general-purpose computer on which a software program that provides a function of a database management system (DBMS) is installed. The image server 5 comprises a storage in which the image DB 6 is configured. This storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the imaging apparatus 2, the image server 5 prepares the medical image in a format for a database and registers the medical image in the image DB 6.

Image data of the medical image acquired by the imaging apparatus 2 and accessory information are registered in the image DB 6. The accessory information includes, for example, an image identification (ID) for identifying each medical image, a patient ID for identifying a subject, an examination ID for identifying an examination, a unique ID (unique identification (UID)) allocated for each medical image, examination date and examination time at which a medical image is generated, the type of imaging apparatus used in an examination for acquiring a medical image, patient information such as the name, age, and gender of a patient, an examination part (an imaging part), imaging information (an imaging protocol, an imaging sequence, an imaging method, imaging conditions, the use of a contrast medium, and the like), and information such as a series number or a collection number in a case where a plurality of medical images are acquired in one examination.

In addition, in a case where the viewing request from the interpretation WS 3 and the medical care WS 4 is received through the network 10, the image server 5 searches for a medical image registered in the image DB 6 and transmits the searched for medical image to the interpretation WS 3 and to the medical care WS 4 that are request sources.

In the present embodiment, it is assumed that the medical image is a three-dimensional CT image consisting of a plurality of tomographic images with a lung as a diagnosis target, and an interpretation report on a structure of interest such as an abnormal shadow included in the lung is created by interpreting the CT image in the interpretation WS 3. The medical image is not limited to the CT image, and any medical image such as an MRI image and a simple two-dimensional image acquired by a simple X-ray imaging apparatus can be used.

The report server 7 incorporates a software program for providing a function of a database management system to a general-purpose computer. In a case where the report server 7 receives a request to register the interpretation report from the interpretation WS 3, the report server 7 prepares the interpretation report in a format for a database and registers the interpretation report in the report DB 8.

In the report DB 8, an interpretation report including the comments on findings created by the radiologist using the interpretation WS 3 is registered. The interpretation report may include, for example, information such as a medical image to be interpreted, an image ID for identifying the medical image, a radiologist ID for identifying the radiologist who performed the interpretation, a lesion name, lesion position information, information for accessing a medical image (which will be described in detail later), and property information (which will be described in detail later).

Further, in a case where the report server 7 receives the viewing request for the interpretation report from the interpretation WS 3 and the medical care WS 4 through the network 10, the report server 7 searches for the interpretation report registered in the report DB 8, and transmits the searched for interpretation report to the interpretation WS 3 and to the medical care WS 4 that are request sources.

The network 10 is a wired or wireless local area network that connects various apparatuses in a hospital to each other. In a case where the interpretation WS 3 is installed in another hospital or clinic, the network 10 may be configured to connect local area networks of respective hospitals through the Internet or a dedicated line.

Figure 2:
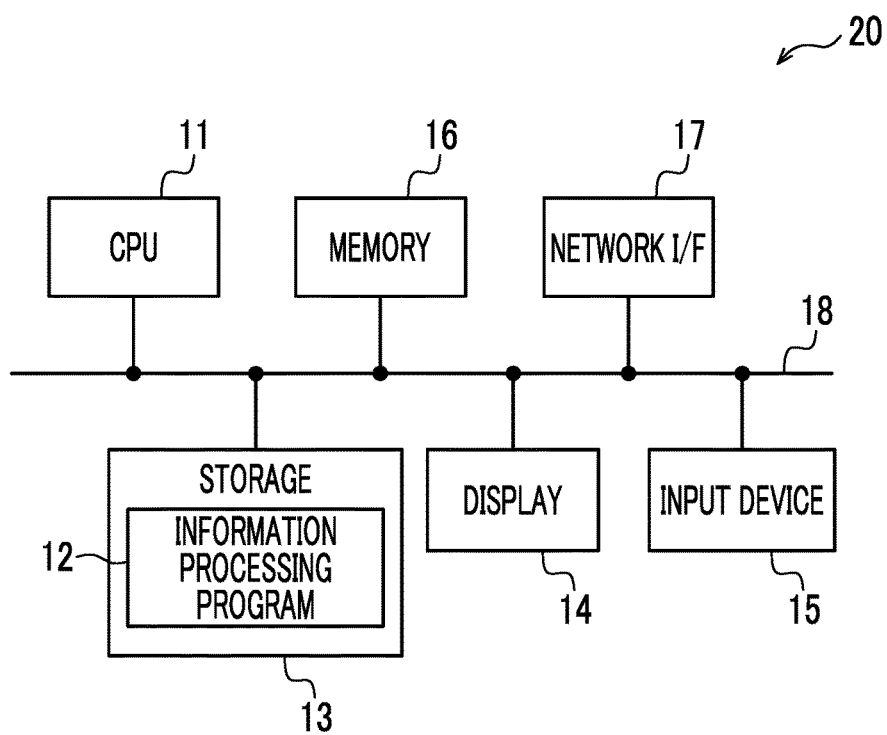
FIG. 2 is a diagram showing a schematic configuration of the information processing apparatus according to the first embodiment.

Next, the information processing apparatus according to the first embodiment will be described. FIG. 2 describes a hardware configuration of the information processing apparatus according to the first embodiment of the present disclosure. As shown in FIG. 2, the information processing apparatus 20 includes a central processing unit (CPU) 11, a non-volatile storage 13, and a memory 16 as a temporary storage area. Further, the information processing apparatus 20 includes a display 14 such as a liquid crystal display, an input device 15 such as a keyboard and a mouse, and a network interface (I/F) 17 connected to the network 10. The CPU 11, the storage 13, the display 14, the input device 15, the memory 16, and the network I/F 17 are connected to a bus 18. The CPU 11 is an example of a processor in the present disclosure.

The storage 13 is realized by a hard disk drive (HDD), a solid state drive (SSD), a flash memory, and the like. An information processing program 12 is stored in the storage 13 as the storage medium. The CPU 11 reads out the information processing program 12 from the storage 13, loads the read-out program into the memory 16, and executes the loaded information processing program 12.

Figure 3:
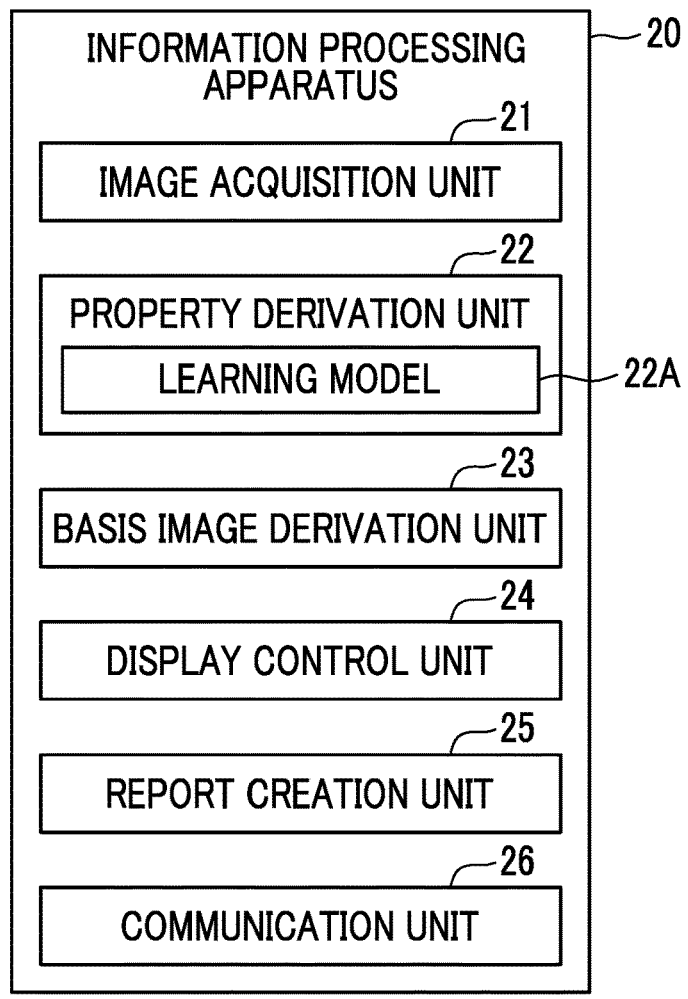
FIG. 3 is a functional configuration diagram of the information processing apparatus according to the first embodiment.

Next, a functional configuration of the information processing apparatus according to the first embodiment will be described. FIG. 3 is a diagram showing a functional configuration of the information processing apparatus according to the present embodiment. As shown in FIG. 3, the information processing apparatus 20 comprises an image acquisition unit 21, a property derivation unit 22, a basis image derivation unit 23, a display control unit 24, a report creation unit 25, and a communication unit 26. Then, in a case where the CPU 11 executes the information processing program 12, the CPU 11 functions as the image acquisition unit 21, the property derivation unit 22, the basis image derivation unit 23, the display control unit 24, the report creation unit 25, and the communication unit 26.

The image acquisition unit 21 acquires a medical image for creating an interpretation report from the image server 5 according to an instruction from the input device 15 by the radiologist who is an operator.

The property derivation unit 22 analyzes the medical image to derive property information indicating a property for at least one property item which is related to the structure of interest such as an abnormal shadow candidate included in the medical image. In the present embodiment, the medical image is a three-dimensional image consisting of a plurality of tomographic images. The property derivation unit 22 analyzes each of the plurality of tomographic images to derive property information. For this purpose, the property derivation unit 22 has a learning model 22A in which machine learning is performed to discriminate the structure of interest in the medical image and to discriminate the property for at least one property item which is related to the discriminated structure of interest. In the present embodiment, the learning model 22A includes a convolutional neural network (CNN) in which deep learning is performed using supervised training data so as to discriminate whether or not each pixel (voxel) in the medical image represents a structure of interest, and to discriminate a property for at least one property item in a case where the pixel represents a structure of interest.

Figure 4:
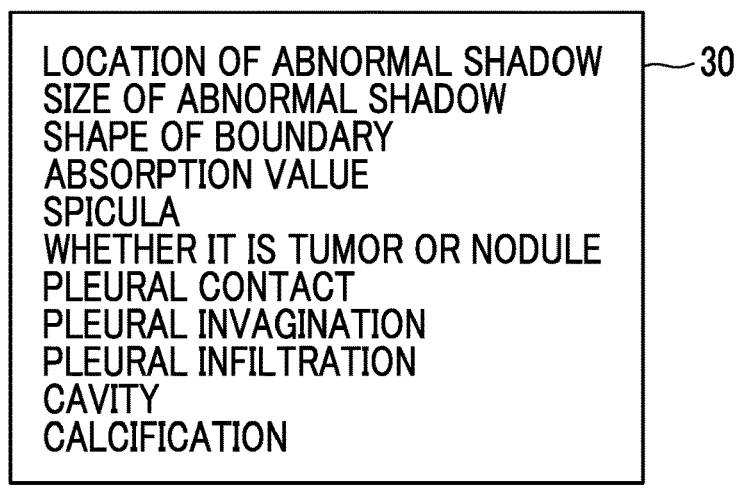
FIG. 4 is a diagram showing an example of property information.

FIG. 4 is a diagram showing an example of property information discriminated by the learning model 22A of the property derivation unit 22. In the present embodiment, it is assumed that the structure of interest for discriminating the property is a lung nodule, and property information 30 indicates properties for a plurality of property items for the lung nodule. For example, as the property items, the location of the abnormal shadow (that is, lung nodule), the size of the abnormal shadow, the shape of the boundary (clear, irregular, and lobular), the type of absorption value (solid and frosted glass type), the presence or absence of spicula, whether it is a tumor or a nodule, the presence or absence of pleural contact, the presence or absence of pleural invagination, the presence or absence of pleural infiltration, the presence or absence of a cavity, and the presence or absence of calcification are used. The property is the result of having or not having each property item. Further, regarding the property items of the location of the abnormal shadow, the size of the abnormal shadow, the shape of the boundary, the type of absorption value, and whether it is a tumor or a nodule, the location, size, and type discriminated by the learning model 22A are the properties. The learning model 22A is constructed by training a neural network using a large number of medical images including the structure of interest and a large number of supervised training data whose properties for a plurality of property items which are related to the structure of interest are known.

Note that the learning model for detecting the structure of interest from the medical image and the learning model for detecting the property information of the structure of interest may be constructed separately. Further, the property information derived by the property derivation unit 22 is saved in the storage 13.

Further, as the learning model 22A, any learning model such as, for example, a support vector machine (SVM) can be used in addition to the convolutional neural network.

Figure 5:
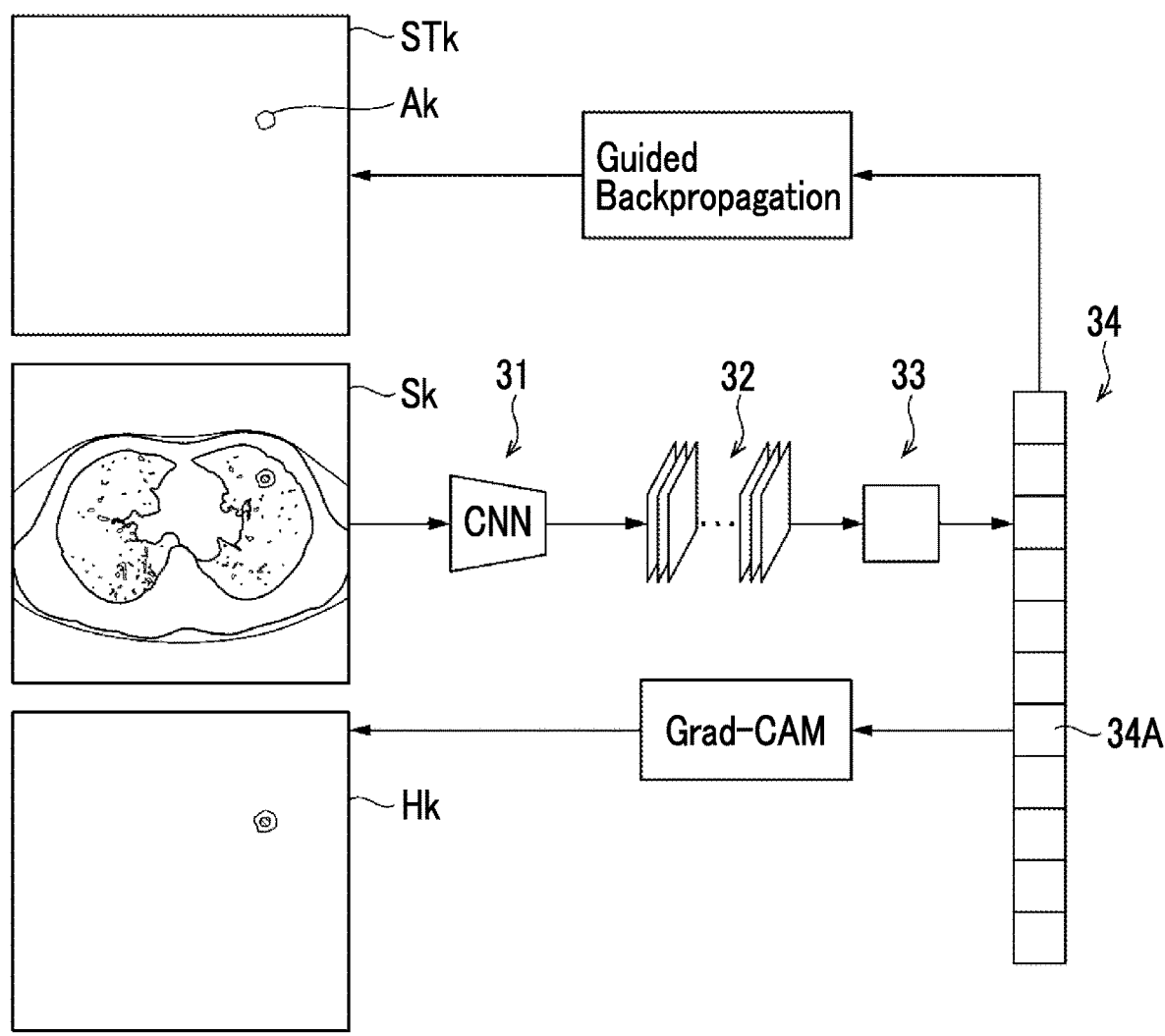
FIG. 5 is a conceptual diagram of derivation of property information and derivation of a basis image performed by a learning model in the first embodiment.

The basis image derivation unit 23 uses the method described in Non-Patent Document 1 to specify, in the medical image, a basis region serving as a basis for deriving the property related to the structure of interest, and derives a basis image in which the basis region is specified. In the present embodiment, the basis image derivation unit 23 derives the basis image using the property information derived by the learning model 22A of the property derivation unit 22. FIG. 5 is a conceptual diagram of derivation of property information and derivation of a basis image performed by the learning model 22A in the first embodiment. Note that FIG. 5 shows processing for one tomographic image Sk among a plurality of tomographic images Si (i=1 to n: n is the number of tomographic images) included in the medical image.

First, the learning model 22A of the property derivation unit 22 derives a feature map 32 of the tomographic image Sk via a CNN 31, inputs the feature map 32 into a fully connected layer 33, and derives property information 34 indicating the properties for the property items which are related to the structure of interest. Note that each square of the property information 34 represents an output (that is, a probability score) representing the property in each of the property items. Here, a property 34A for one property item in the property information 34 will be examined.

The basis image derivation unit 23 specifies, in the feature map 32, a portion having a large influence on the probability score of the property 34A by differentiating the intensity in the feature map, and derives a heat map Hk representing its size via the method of Grad-CAM described in Non-Patent Document 1.

On the other hand, the basis image derivation unit 23 uses the Guided Backpropagation method described in Non-Patent Document 1 to specify a region having a large probability score, which serves as a basis for specifying the property 34A, as a basis region by backpropagating the CNN 31, and derives a specific image STk. Specifically, the basis image derivation unit 23 performs backpropagation with respect to the feature map 32, setting the value of a pixel other than a pixel whose feature amount is active on the map, that is, a pixel having a positive pixel value to 0. Backpropagation corresponds to reverse convolution of the convolution in the CNN 31. Accordingly, only the portion that affects the activity in the feature map 32 is restored with the same resolution as the tomographic image Sk input to the CNN 31. The restored portion is a basis region Ak. Further, an image including the basis region Ak and having the same resolution as the tomographic image Sk input to the CNN 31 is the specific image STk. Accordingly, the specific image STk includes the basis region Ak that specifies the property 34A at the same resolution as the tomographic image Sk.

The basis image derivation unit 23 derives a specific image STi for all tomographic images Si for one property 34A. In addition, in FIG. 5, only one specific image STk including the basis region Ak is shown. Then, the basis image derivation unit 23 selects a specific image STi including a basis region Ai that most prominently represents the property 34A from the plurality of specific images STi, and selects a tomographic image corresponding to the selected specific image from the plurality of tomographic images Si, thereby deriving the basis image. Here, "most prominently represents" means that the size of the basis region Ai is the largest, or that the probability score in the basis region Ai is the largest.

Figure 6:
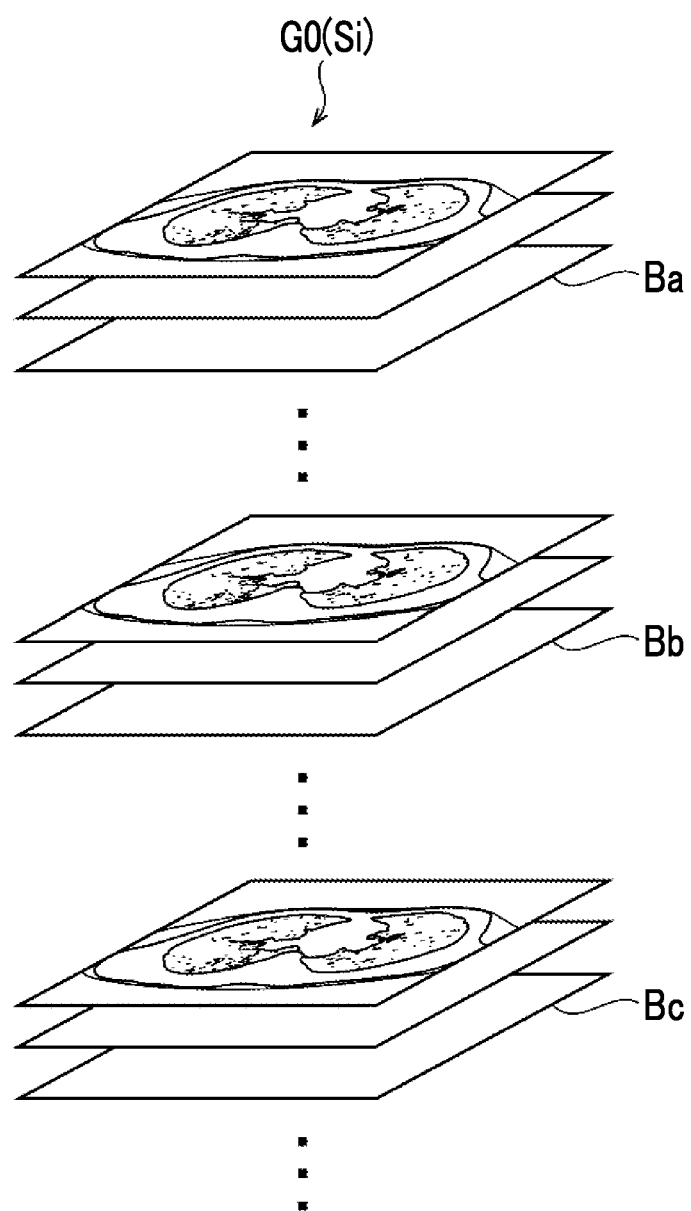
FIG. 6 is a diagram for describing selection of basis images.

FIG. 6 is a diagram for describing the selection of basis images. In FIG. 6, basis images Ba, Bb, and Bc are selected from the plurality of tomographic images Si included in a medical image G0 for the three properties of solidity, spicula, and lobulation.

Figure 7:
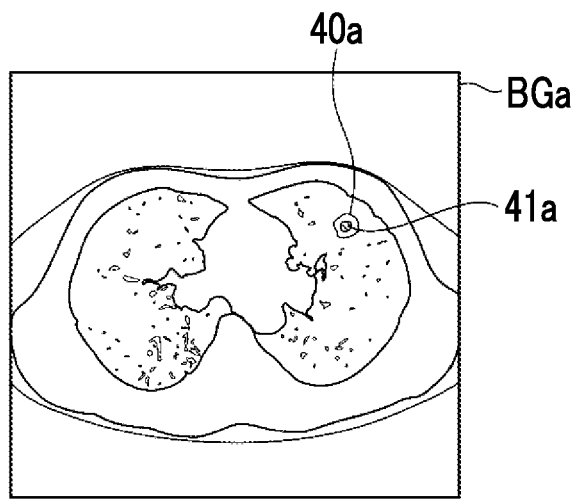
FIG. 7 is a diagram showing emphasized basis images.
Figure 7:
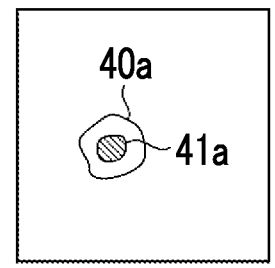
Figure 7:
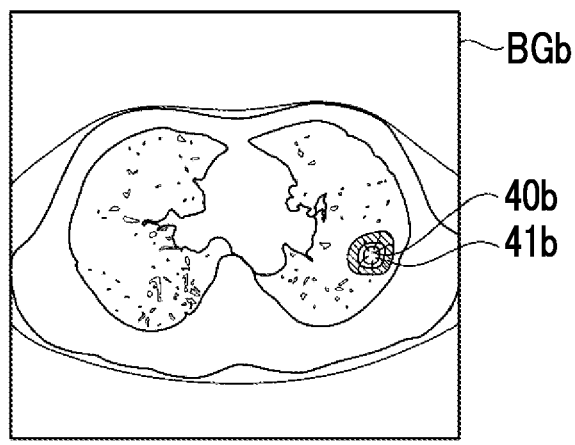
Figure 7:
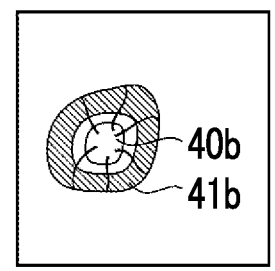
Figure 7:
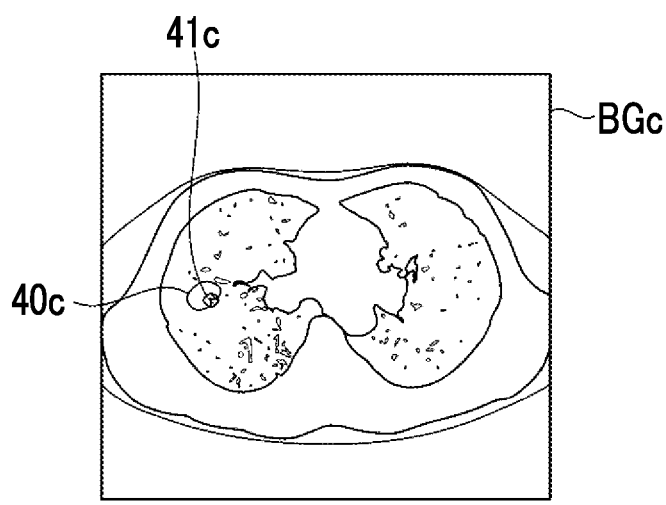
Figure 7:
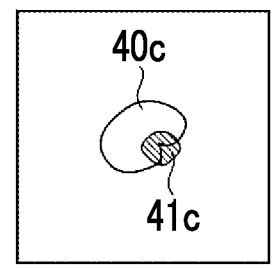

Then, the basis image derivation unit 23 combines the basis images Ba, Bb, and Bc and the tomographic images corresponding to each of the basis images Ba, Bb, and Bc to derive an emphasized basis image in which the basis region in the tomographic image is emphasized. FIG. 7 is a diagram showing emphasized basis images. FIG. 7 shows enlarged views of the regions of the structure of interest included in emphasized basis images BGa, BGb, and BGc on the right side of the emphasized basis images BGa, BGb, and BGc. As shown in FIG. 7, in the emphasized basis image BGa of the solidity, a solid tumor 40a is included, and a heat map 41a for emphasizing the solid tumor 40a is added near the center thereof. The region of the heat map 41a corresponds to the basis region in the basis image. In FIG. 7, the heat map is shown by diagonal lines for the sake of simplification. Further, in the emphasized basis image BGb of the spicula, a tumor 40b with the spicula is included, and a heat map 41b for emphasizing the spicula is added to the portion of the spicula. In the emphasized basis image BGc of the lobulation, a lobular tumor 40c is included, and a heat map 41c for emphasizing the lobulated portion is added thereto.

Figure 8:
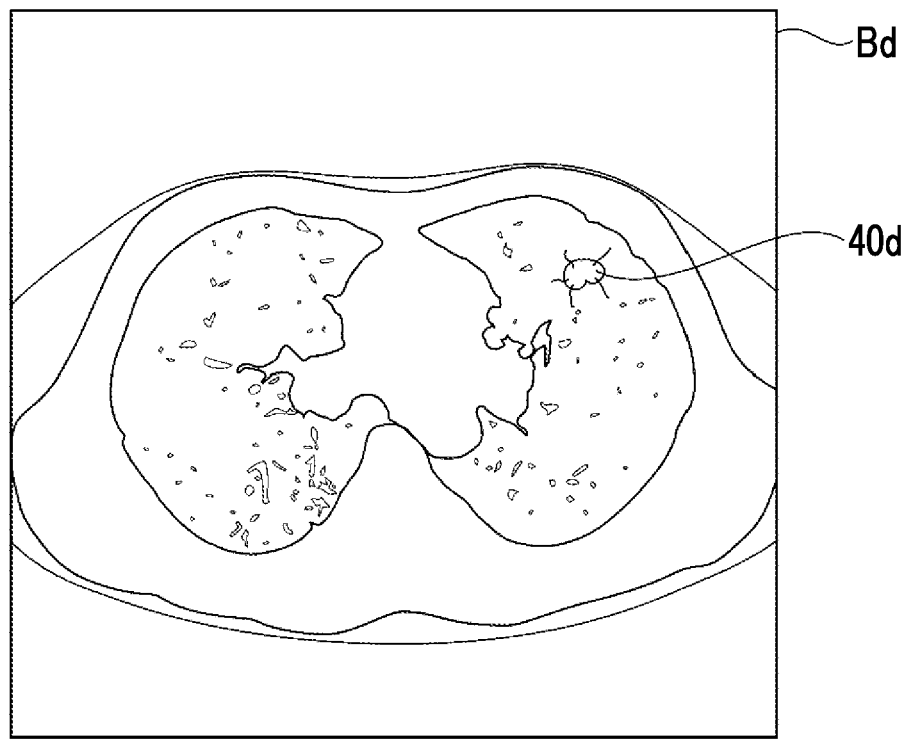
FIG. 8 is a diagram showing a basis image.
Figure 9:
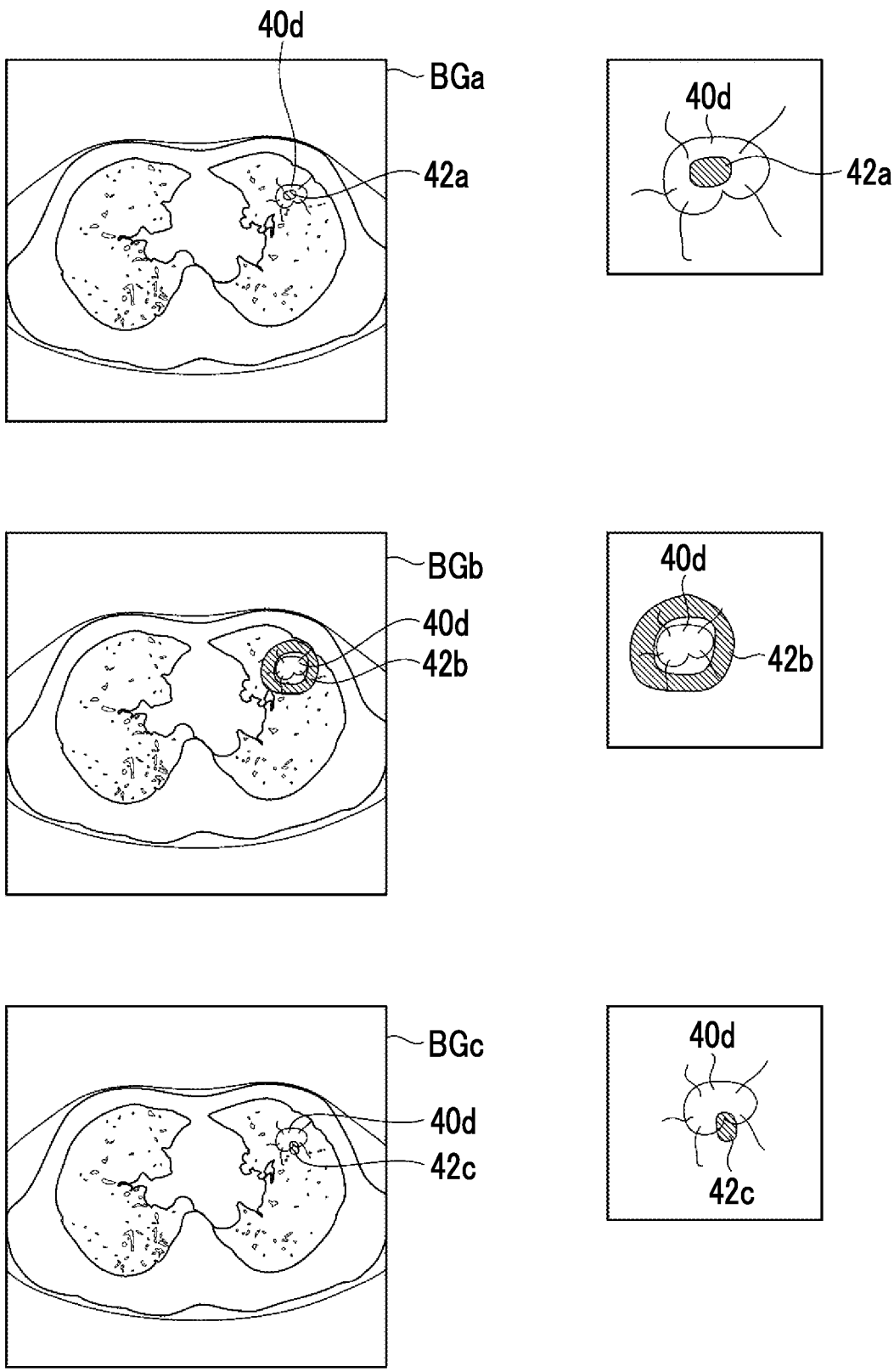
FIG. 9 is a diagram showing emphasized basis images.

In addition, one basis image may be selected for a plurality of types of property items. For example, as shown in FIG. 8, a specific image including a lobular solid tumor 40d with spicula as a basis region may be selected as a basis image Bd. In such a case, as shown in FIG. 9, the basis image derivation unit 23 derives three emphasized basis images BGa to BGc in which each of the solidity, the spicula, and the lobulation is emphasized. As shown in FIG. 9, in the emphasized basis image BGa of the solidity, a heat map 42a for emphasizing the solidity is added near the center of the tumor 40d. Further, in the emphasized basis image BGb of the spicula, a heat map 42b for emphasizing the spicula is added to the portion of the spicula in the tumor 40d. In the emphasized basis image BGc of the lobulation, a heat map 42c for emphasizing the lobulated portion in the tumor 40d is added thereto. FIG. 9 also shows enlarged views of the regions of the structure of interest in emphasized basis images BGa, BGb, and BGc on the right side of the emphasized basis images BGa, BGb, and BGc.

Figure 10:
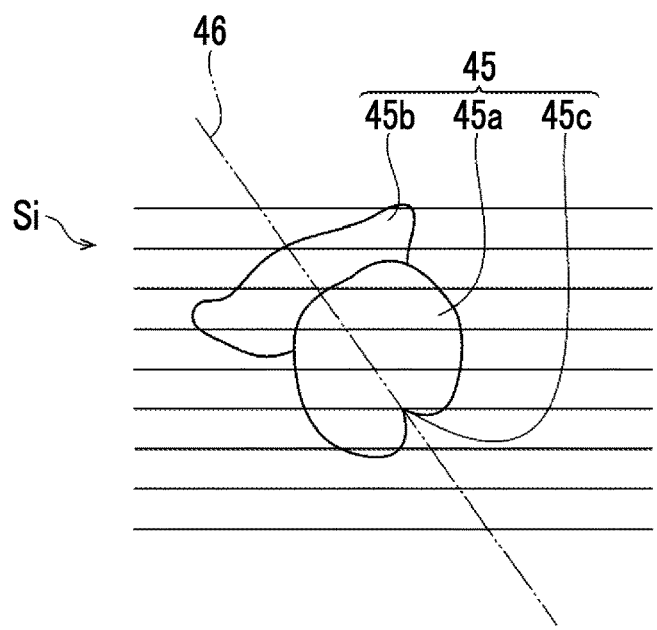
FIG. 10 is a diagram for describing generation of an oblique image.

On the other hand, a basis region serving as a basis for specifying the property for a certain property item may be included over a plurality of tomographic images. In this case, in a case where the basis region in a plurality of tomographic images is observed three-dimensionally, a tomographic plane in which the property of the property item appears most prominently may be specified, and a tomographic image (that is, an oblique image) on the tomographic plane may be derived as a basis image. FIG. 10 is a diagram for describing generation of an oblique image. As shown in FIG. 10, it is assumed that a lobular solid tumor 45 with spicula is present over a plurality of tomographic images Si. The tumor 45 includes a solid portion 45a, a spicula portion 45b, and a lobular portion 45c. In such a case, on a tomographic plane 46 passing through all of the solid portion 45a, the spicula portion 45b, and the lobular portion 45c, all of the solid portion 45a, the spicula portion 45b, and the lobular portion 45c are most easily observed. Therefore, the basis image derivation unit 23 sets the tomographic plane 46 that most prominently represents a plurality of properties in the medical image G0, and derives the oblique image on the tomographic plane 46 as the basis image. A maximum value emphasized image (maximum intensity projection (MIP) image) in a case where the viewpoint is placed in the direction orthogonal to the tomographic plane 46 may be derived as the basis image.

The display control unit 24 displays the emphasized basis image on the display 14. In the present embodiment, the display control unit 24 displays a report creation screen for creating an interpretation report for the medical image G0 on the display 14, and displays an emphasized basis image on the report creation screen in response to an operator's instruction.

Figure 11:
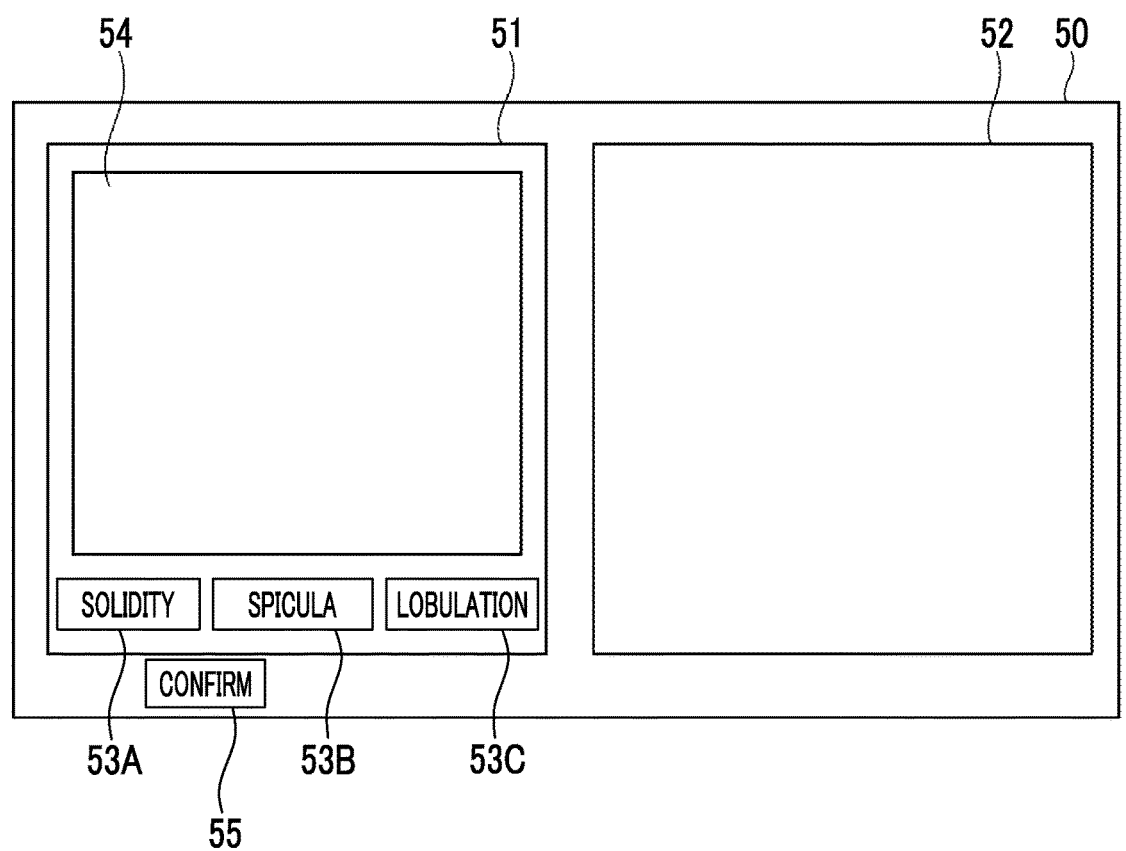
FIG. 11 is a diagram showing a report creation screen in the first embodiment.

FIG. 11 is a diagram showing a report creation screen in the first embodiment. As shown in FIG. 11, a report creation screen 50 includes a sentence display region 51 and an image display region 52. In the sentence display region 51, designation buttons 53A to 53C for designating the property items derived in the medical image G0 are displayed. In the present embodiment, for the sake of simplicity of description, only three designation buttons 53A to 53C regarding solidity, spicula, and lobulation among the plurality of property items are displayed. In the sentence display region 51, a findings input region 54 is included above these designation buttons 53A to 53C. Further, below the sentence display region 51, a confirmation button 55 for confirming the input comments on findings is displayed.

Figure 12:
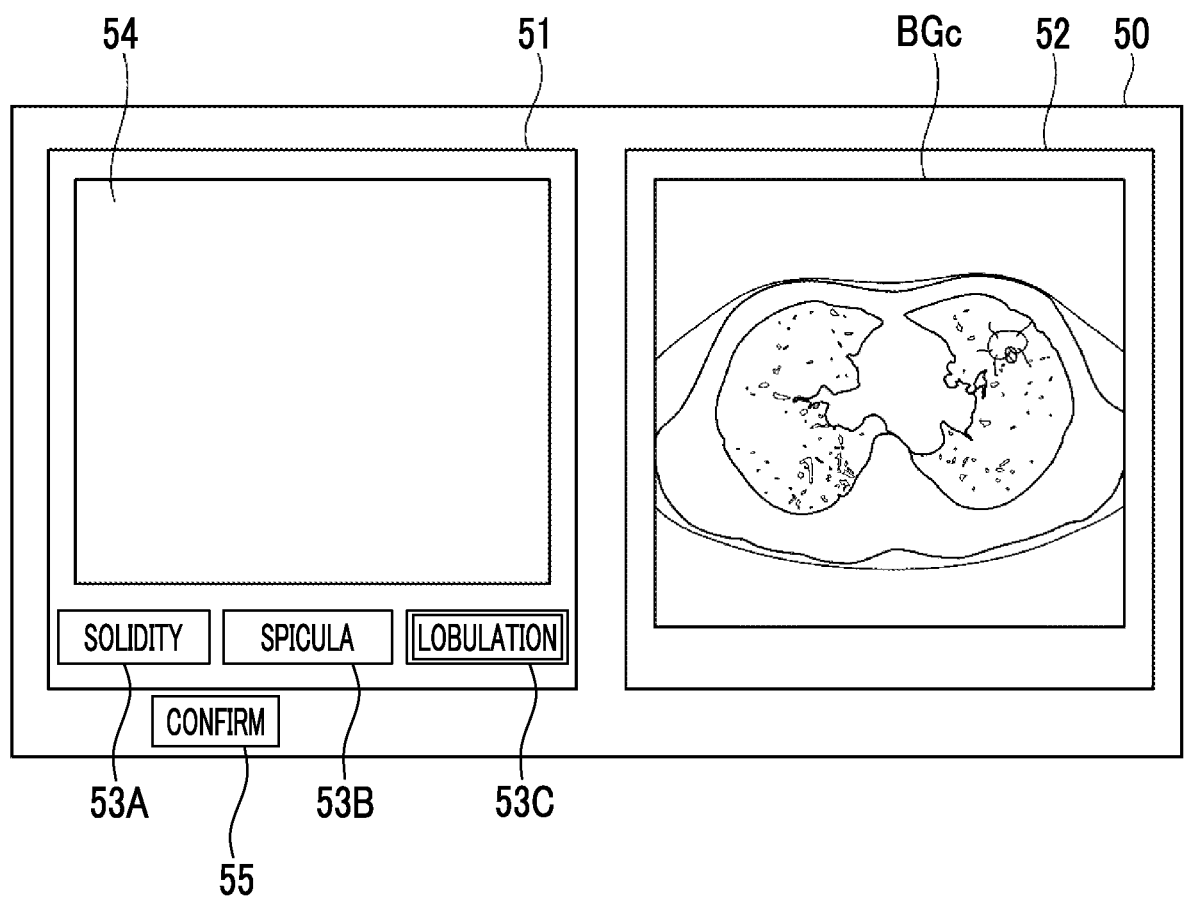
FIG. 12 is a diagram showing the report creation screen in the first embodiment.

Then, in a case where the operator selects any of the designation buttons 53A to 53C on the report creation screen 50, the display control unit 24 displays an emphasized basis image for the property item corresponding to the selected designation button in the image display region 52. For example, in a case where the designation button 53C for lobulation is selected, the display control unit 24 displays the emphasized basis image BGc shown in FIG. 9 in the image display region 52 as shown in FIG. 12. FIG. 12 shows that the designation button 53C is selected by adding a frame to the designation button 53C.

The report creation unit 25 creates an interpretation report. In creating the interpretation report, the operator inputs the comments on findings in the findings input region 54 using the input device 15 while looking at the emphasized basis image displayed in the image display region 52. The report creation unit 25 transcribes the comments on findings input in the findings input region 54 into an interpretation report to create an interpretation report. Then, in a case where the confirmation button 55 is selected, the report creation unit 25 saves the created interpretation report in the storage 13 together with one or more emphasized basis images referred to in the case where the comments on findings are input.

The communication unit 26 transmits the created interpretation report to the report server 7 via the network I/F 17 together with one or more emphasized basis images referred to in the case where the comments on findings are input. In the report server 7, the created interpretation report is saved together with one or more emphasized basis images referred to in the case where the comments on findings are input.

Figure 13:
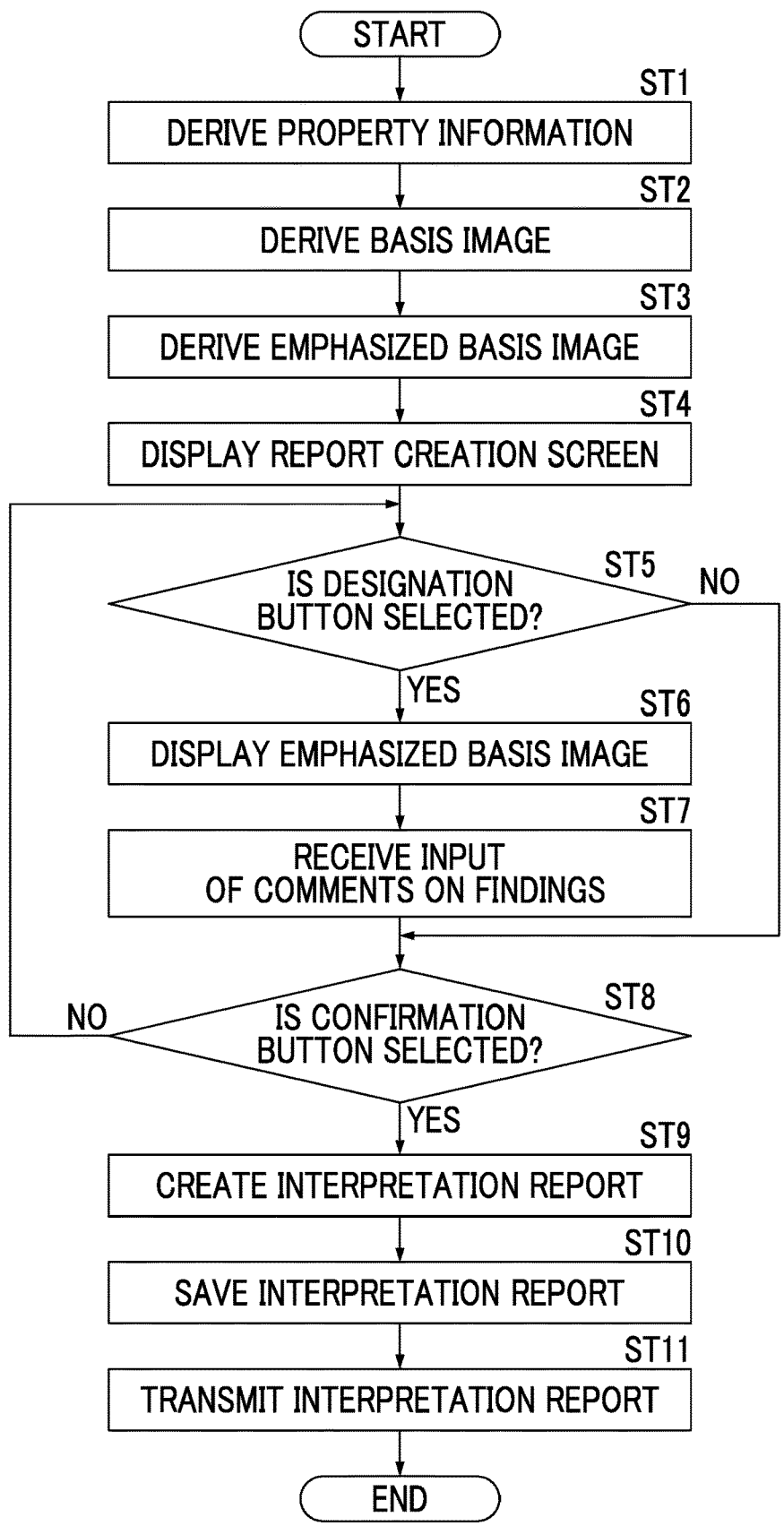
FIG. 13 is a flowchart showing a process performed in the first embodiment.

Next, a process performed in the first embodiment will be described. FIG. 13 is a flowchart showing a process performed in the first embodiment. It is assumed that the medical image to be interpreted is acquired from the image server 5 by the image acquisition unit 21 and is saved in the storage 13. The process is started in a case where an instruction to create an interpretation report is given by the radiologist, and the property derivation unit 22 derives property information indicating the properties for at least one predetermined property item which is related to the structure of interest included in the medical image G0 (Step ST1). Next, the basis image derivation unit 23 specifies the basis region serving as a basis for deriving the property related to the structure of interest for each property item, and derives the basis image including the basis region (Step ST2). Further, the basis image derivation unit 23 emphasizes the basis region in the basis image and derives the emphasized basis image (Step ST3).

Subsequently, the display control unit 24 displays the report creation screen 50 on the display 14 (Step ST4). Then, in a case where any of the designation buttons 53A to 53C is selected (Step ST5; YES), the display control unit 24 displays the emphasized basis image corresponding to the selected designation button in the image display region 52 (Step ST6). In a case where Step ST5 is negative, the process proceeds to Step ST8, which will be described later. Subsequently, the report creation unit 25 receives the input of the comments on findings to the findings input region 54 (Step ST7), and starts monitoring whether or not the confirmation button 55 is selected (Step ST8). In a case where Step ST8 is negative, the process returns to Step ST5, and the processes after Step ST5 are repeated.

In a case where Step ST8 is affirmative, the report creation unit 25 creates an interpretation report including the input comments on findings (Step ST9), and saves the created interpretation report in the storage 13 together with one or more emphasized basis images referred to in the case where the comments on findings are input (Step ST10). Further, the communication unit 26 transmits the created interpretation report to the report server 7 together with one or more emphasized basis images referred to in the case where the comments on findings are input (Step ST11), and ends the process.

In this way, in the first embodiment, the basis region serving as a basis for deriving the property in the medical image G0 is specified for each of the derived property items, and the basis image including the basis region is derived. Therefore, by displaying and referring to the basis image, it is possible to recognize the region serving as a basis from which the property for the property item of the structure of interest included in the basis image is derived.

Further, by deriving the emphasized basis image in which the basis region is emphasized in the basis image, it is possible to easily recognize the portion serving as a basis from which the property for the property item of the structure of interest included in the basis image is derived.

In addition, by generating an oblique image or an MIP image on the tomographic plane where the oblique image is generated from a plurality of tomographic images as the basis image, it is possible to make it easier to see the basis region serving as a basis for deriving properties in a region of interest in the basis image.

Figure 14:
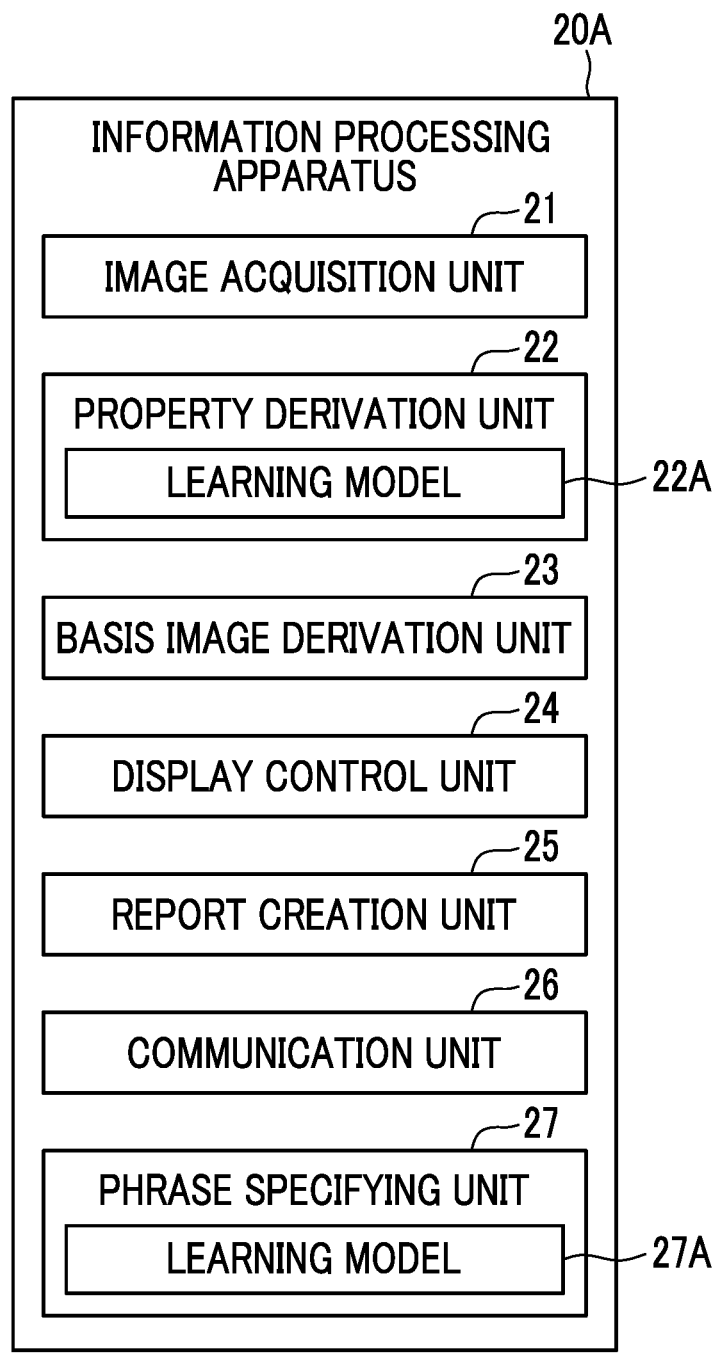
FIG. 14 is a functional configuration diagram of an information processing apparatus according to the second embodiment.

Next, a second embodiment of the present disclosure will be described. FIG. 14 is a diagram showing a functional configuration of an information processing apparatus according to the second embodiment of the present disclosure. In FIG. 14, the same reference numerals are assigned to the same configurations as those in FIG. 3, and detailed description thereof will be omitted here. An information processing apparatus 20A according to the second embodiment is different from that of the first embodiment in that it further comprises a phrase specifying unit 27 that analyzes the comments on findings input by the operator to specify a phrase related to the property item included in the comments on findings, and the display control unit 24 adds information for accessing the basis image serving as a basis for deriving the properties represented by the specified phrase to the phrase specified in the comments on findings, and displays the comments on findings on the display 14.

The phrase specifying unit 27 specifies a phrase related to a property item included in the comments on findings input to the findings input region 54. For this purpose, the phrase specifying unit 27 has a learning model 27A in which machine learning is performed to specify a phrase related to a property item included in a sentence. In the present embodiment, the learning model 27A consists of a convolutional neural network (CNN) in which deep learning is performed using the supervised training data so as to discriminate phrases related to property items included in the input comments on findings in a case where the comments on findings are input.

The supervised training data for training the learning model 27A includes sentences and phrases related to property items included in the sentences. For example, a sentence "A solid tumor with a clear boundary is found in the lower lobe S6 of the left lung", and "lower lobe S6 of the left lung", "clear boundary", "solid", and "tumor" which are phrases related to the property items are included. The learning model 27A is constructed by training a neural network using a large amount of such supervised training data. Accordingly, in a case where the sentence "A solid tumor with a clear boundary is found in the lower lobe S6 of the left lung" is input, the learning model 27A is trained to output "lower lobe S6 of the left lung", "clear boundary", "solid", and "tumor" as the phrases related to the property items.

Further, as the learning model 27A, for example, any learning model such as a support vector machine and a recurrent neural network can be used, in addition to the convolutional neural network.

In addition, the phrase specifying unit 27 adds information for accessing the basis image serving as a basis for deriving the properties represented by the specified phrase to the phrase specified in the comments on findings. Then, in a case where the phrase to which the information for accessing the basis image is added is selected, the display control unit 24 displays the basis image corresponding to the selected phrase on the display 14.

Figure 15:
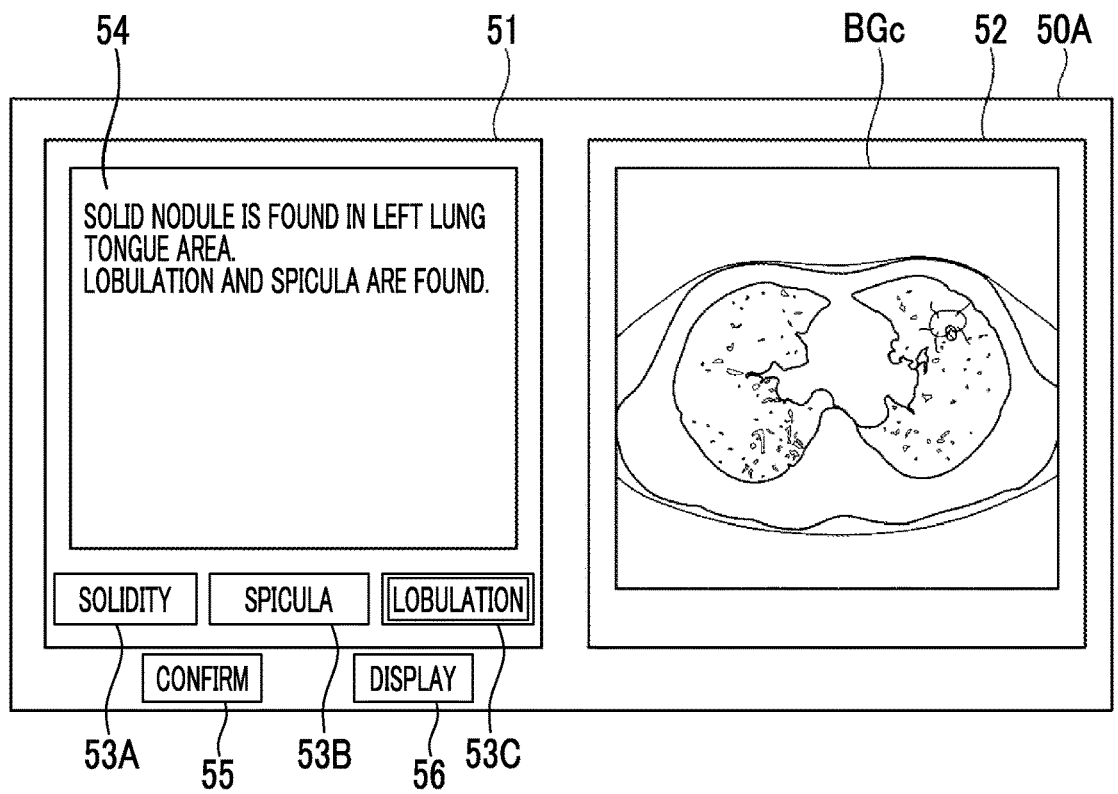
FIG. 15 is a diagram showing a report creation screen in the second embodiment.

FIG. 15 is a diagram showing a report creation screen in the second embodiment. As shown in FIG. 15, a report creation screen 50A in the second embodiment includes the sentence display region 51 and the image display region 52, similarly to the report creation screen 50 in the first embodiment. In the sentence display region 51, the designation buttons 53A to 53C and the findings input region 54 are included. A display button 56 is displayed below the sentence display region 51. In the findings input region 54, comments on findings "A solid nodule is found in the left lung tongue area. Lobulation and spicula are found" are input.

Figure 16:
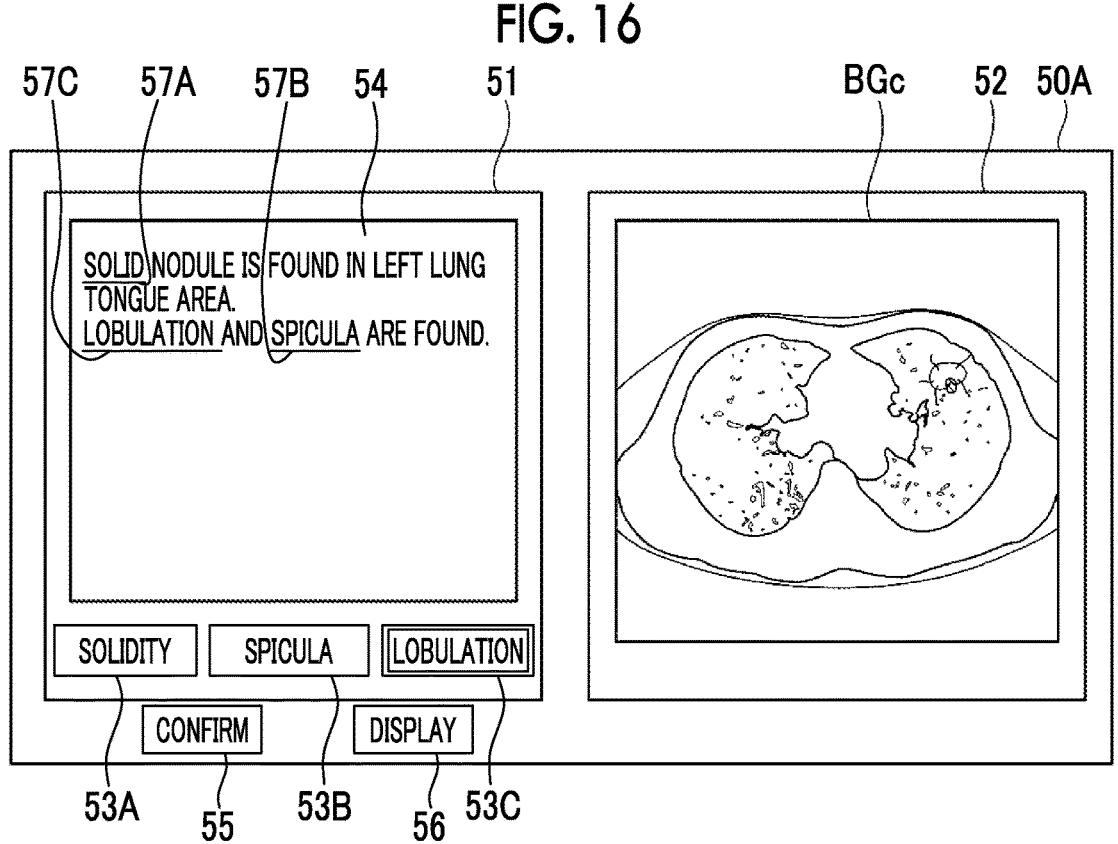
FIG. 16 is a diagram showing the report creation screen in the second embodiment.

In the second embodiment, in a case where the display button 56 is selected, for example, after inputting the comments on findings, the phrase specifying unit 27 specifies the phrase related to the property item included in the comments on findings. Then, the phrase specifying unit 27 adds information for accessing the basis image serving as a basis for deriving the properties represented by the specified phrase to the specified phrase. In the second embodiment, as an example of the information for accessing the basis image, the phrase specifying unit 27 embeds a hyperlink in the phrase. FIG. 16 is a diagram showing a state in which a hyperlink is embedded. As shown in FIG. 16, the display control unit 24 embeds a hyperlink 57A for the emphasized basis image BGa of the solidity in the phrase "solid" in the comments on findings "A solid nodule is found in the left lung tongue area. Lobulation and spicula are found". Further, the phrase specifying unit 27 embeds a hyperlink 57B to the emphasized basis image BGb of the spicula in the phrase "spicula". Moreover, the phrase specifying unit 27 embeds a hyperlink 57C to the emphasized basis image BGc of the lobulation in the phrase "lobulation".

Figure 17:
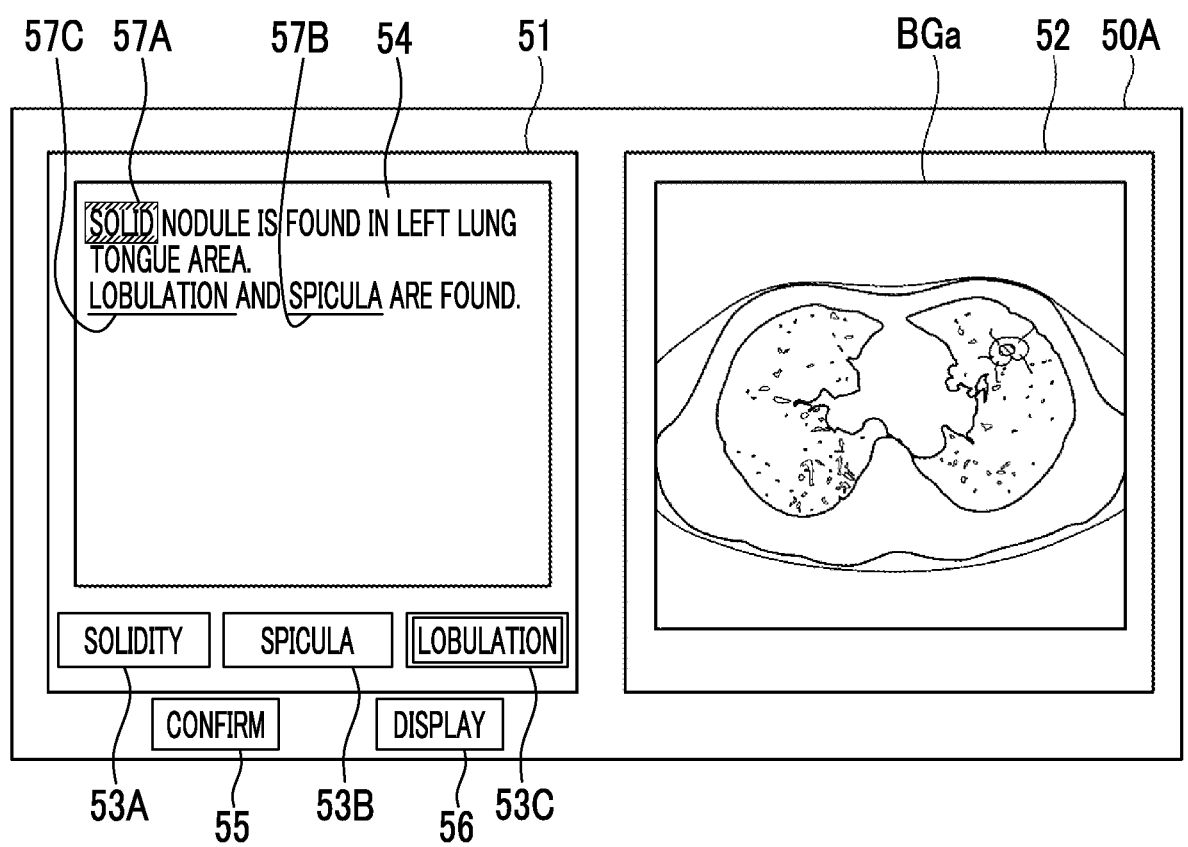
FIG. 17 is a diagram showing the report creation screen in the second embodiment.

In a case where the phrase "solid" in the comments on findings is selected, the display control unit 24 displays the emphasized basis image BGa of the solidity in the image display region 52 as shown in FIG. 17. In FIG. 17, hatching is added to the selected phrase.

The hyperlinks 57A to 57C may include a uniform resource locator (URL) indicating a storage location of the emphasized basis images BGa to BGc. Here, the interpretation report is saved in the report server 7 together with the emphasized basis image. Therefore, by acquiring information on the storage location in the report server 7 in advance, the storage location in the report server 7 may be included in the hyperlinks 57A to 57C. The information for accessing the emphasized basis images BGa to BGc is not limited to the hyperlink, and, for example, the coordinate positions of the emphasized basis images BGa to BGc in the medical image G0 may be used.

Figure 18:
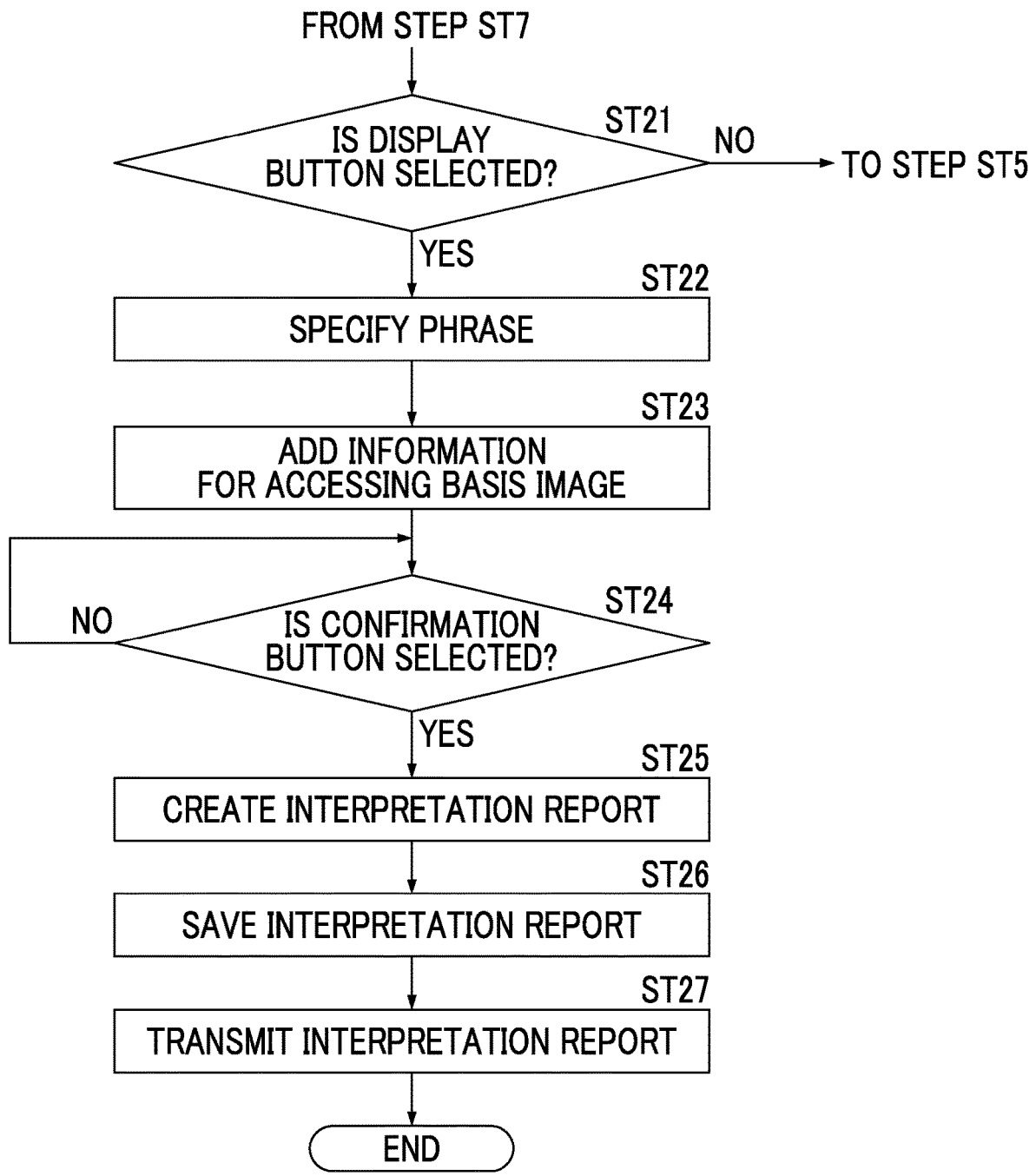
FIG. 18 is a flowchart showing a process performed in the second embodiment.

Next, a process performed in the second embodiment will be described. FIG. 18 is a flowchart showing a process performed in the second embodiment. In the second embodiment, since the processes until the confirmation button 55 is selected are the same as the processes from Step ST1 to Step ST7 in the process of the first embodiment shown in FIG. 13, the processes after Step ST7 in FIG. 13 will be described here.

In a case where the display button 56 is selected on the report creation screen 50A (Step ST21; YES), the phrase specifying unit 27 specifies a phrase related to the property item included in the comments on findings (Step ST22). Further, the phrase specifying unit 27 adds information for accessing the basis image serving as a basis for deriving the properties represented by the specified phrase to the phrase specified in the comments on findings (Step ST23). In a case where Step ST21 is negative, the process returns to Step ST5 in FIG. 13.

Then, monitoring of whether or not the confirmation button 55 is selected is started (Step ST24), and in a case where Step ST24 is affirmative, the report creation unit 25 creates an interpretation report including comments on findings in which information for accessing the basis image is added to the phrase (Step ST25), and saves the created interpretation report in the storage 13 together with one or more emphasized basis images referred to in the case where the comments on findings are input (saving interpretation report, Step ST26). Further, the communication unit 26 transmits the created interpretation report to the report server 7 together with one or more emphasized basis images referred to in the case where the comments on findings are input (Step ST27), and ends the process.

In this way, in the second embodiment, the phrase related to the property item included in the comments on findings is specified, and information for accessing the basis image serving as a basis for deriving the properties represented by the specified phrase is added thereto. Therefore, in a case where a phrase related to a property item included in the comments on findings is selected in the interpretation report, an emphasized basis image corresponding to the selected phrase can be displayed. Therefore, it is possible to immediately check the properties for the structure of interest included in the comments on findings in the emphasized basis image.

Figure 19:
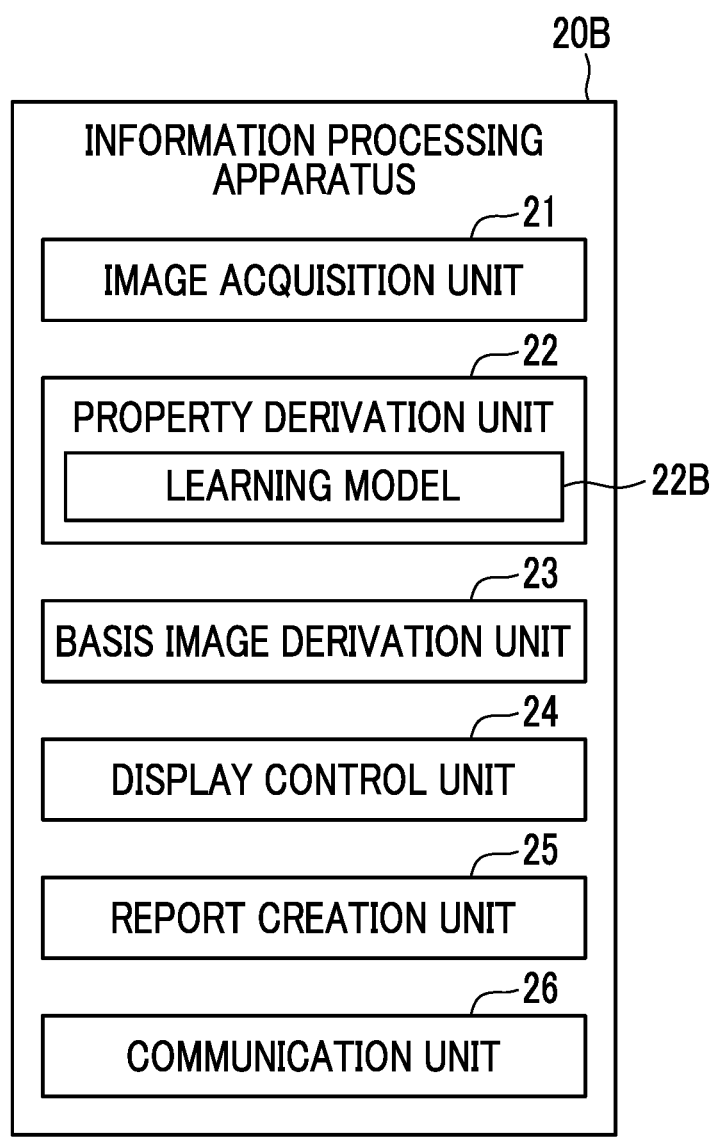
FIG. 19 is a functional configuration diagram of an information processing apparatus according to a third embodiment.

Next, a third embodiment of the present disclosure will be described. FIG. 19 is a diagram showing a functional configuration of an information processing apparatus according to the third embodiment of the present disclosure. In FIG. 19, the same reference numerals are assigned to the same configurations as those in FIG. 3, and detailed description thereof will be omitted here. An information processing apparatus 20B according to the third embodiment is different from that of the first embodiment in that the property derivation unit 22 derives the property for the property item in which a change has occurred with respect to a structure of interest between a first medical image G1 acquired at a first point in time and a second medical image G2 acquired at a second point in time different from the first point in time, and the basis image derivation unit 23 specifies the basis region serving as a basis for deriving the property in at least one of the first medical image G1 or the second medical image G2 and derives the basis image, for the property item in which the change has occurred in the property between the first image and the second image. Note that it is assumed that the time of acquisition of the first medical image G1 is before the time of acquisition of the second medical image G2.

Therefore, the property derivation unit 22 according to the third embodiment has a learning model 22B that has been trained to discriminate the property in which a change has occurred for the structure of interest that is commonly included in two medical images in a case where the two medical images are input. In the third embodiment, the learning model 22B includes a convolutional neural network (CNN) in which deep learning is performed using supervised training data so as to discriminate whether or not each pixel (voxel) in the two medical images represents a structure of interest, and to discriminate changes in the properties of structures of interest in the two medical images in a case where the pixel represents a structure of interest.

In the third embodiment, the basis image derivation unit 23 uses the method described in Non-Patent Document 1 to specify the basis region serving as a basis for deriving the properties in which changes have occurred in the first and second medical images G1 and G2, and derives the basis image including the basis region for each of the first and second medical images G1 and G2. In the third embodiment, the basis image derivation unit 23 derives the basis image using the information derived by the learning model 22B of the property derivation unit 22.

Figure 20:
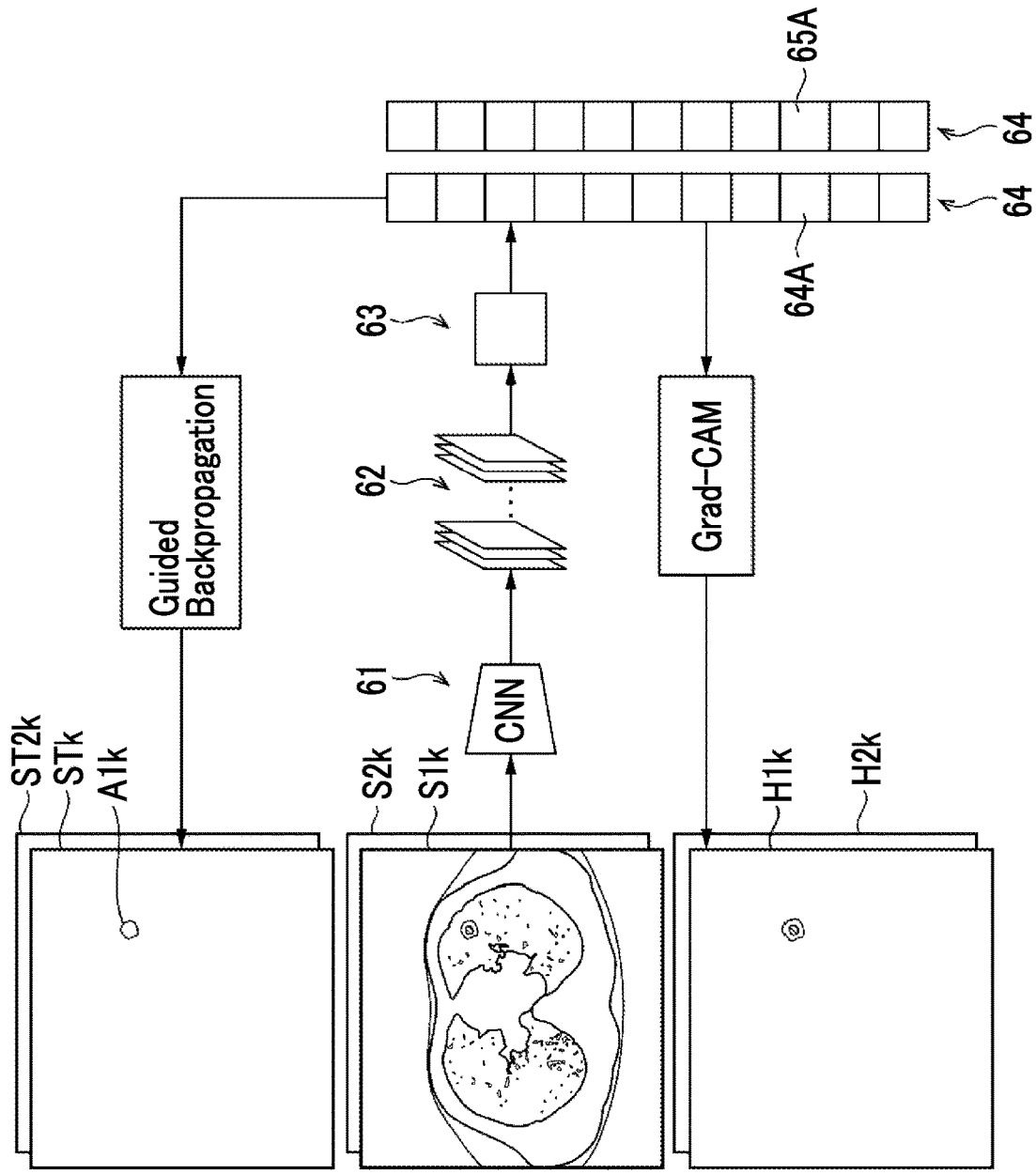
FIG. 20 is a conceptual diagram of derivation of property information and derivation of a basis image performed by a learning model in the third embodiment.

FIG. 20 is a conceptual diagram of derivation of property information and derivation of a basis image performed by the learning model 22B in the third embodiment. Note that FIG. 20 shows processing for one of tomographic images $S1k$ and $S2k$ among a plurality of tomographic images $S1i$ and $S2i$ (i=1 to n: n is the number of tomographic images) included in the first and second medical images G1 and G2, respectively.

First, the learning model 22B of the property derivation unit 22 derives a feature map 62 showing the difference between the tomographic images $S1k$ and $S2k$ via a CNN 61, inputs the feature map 62 into a fully connected layer 63, and derives property information 64 and 65 indicating the properties for the property items in which changes have occurred with respect to the structures of interest included in the tomographic images $S1k$ and $S2k$. Note that each square of the property information 64 represents an output (that is, a probability score) representing the property in each of the property items in which changes have occurred between the tomographic images $S1k$ and $S2k$. Here, properties 64A and 65A for one property item in the property information 64 and 65 will be described.

In the third embodiment, the basis image derivation unit 23 specifies, in the feature map 62, a portion having a large influence on the probability scores of the properties 64A and 65A by differentiating the intensity in the feature map, and derives heat maps representing their sizes for each of the tomographic images $S1k$ and $S2k$ via the method of Grad-CAM described in Non-Patent Document 1 (heat maps $H1k$ and $H2k$).

On the other hand, the basis image derivation unit 23 uses the Guided Backpropagation method described in Non-Patent Document 1 to specify a region having a large probability score, which serves as a basis for specifying the properties 64A and 65A, as a basis region by backpropagating the CNN, and derives specific images $ST1k$ and $ST2k$ for each of the tomographic images $S1k$ and $S2k$. In the specific images $ST1k$ and $ST2k$, basis regions $A1k$ and $A2k$ that specify the properties 64A and 65A are specified at the same resolution as the tomographic images $S1k$ and $S2k$ (only $A1k$ is shown).

The basis image derivation unit 23 derives specific images $ST1i$ and $ST2i$ for all tomographic images $S1i$ and $S2i$ for one property 64A or 65A. In addition, in FIG. 20, only two specific images $ST1k$ and $ST2k$ including the basis regions $A1k$ and $A2k$ are shown. Then, the basis image derivation unit 23 selects specific images $ST1i$ and $ST2i$ including basis regions $A1i$ and $A2i$ that most prominently represent the properties 64A and 65A from the plurality of specific images $ST1i$ and $ST2i$, and selects a tomographic image corresponding to the selected specific image from the plurality of tomographic images $Si$, thereby deriving the basis image.

Figure 21:
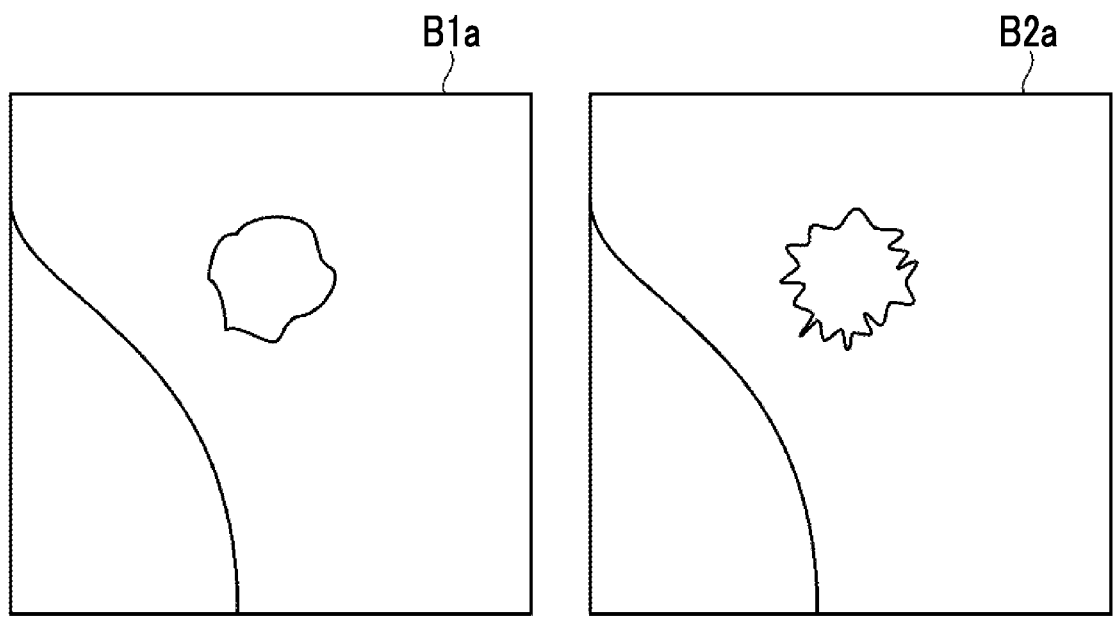
FIG. 21 is a diagram showing basis images in the third embodiment.

FIG. 21 is a diagram showing basis images derived in the third embodiment. In FIG. 21, a first basis image $B1a$ and a second basis image $B2a$ are selected from the first medical image G1 and the second medical image G2, respectively. The basis images $B1a$ and $B2a$ show only a part of the corresponding tomographic image for the sake of description. As shown in FIG. 21, the first basis image $B1a$ includes a solid tumor with a clear boundary, while the second basis image $B2a$ includes the same tumor with an unclear boundary. Therefore, the learning model 22B derives the boundary as the property in which the change has occurred.

Figure 22:
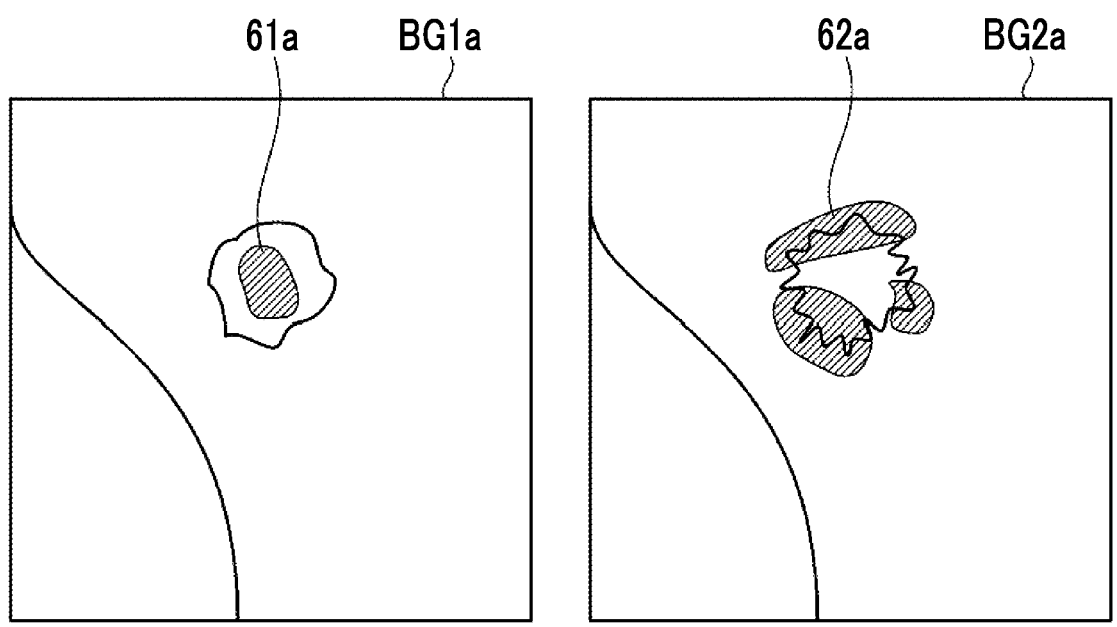
FIG. 22 is a diagram showing emphasized basis images in the third embodiment.

Then, in the third embodiment, the basis image derivation unit 23 combines heat maps $H1a$ and $H1b$ for the first and second basis images $B1a$ and $B2a$ with the first and second basis images $B1a$ and $B2a$, and derives emphasized basis images $BG1a$ and $BG2a$. FIG. 22 is a diagram showing emphasized basis images. As shown in FIG. 22, in the emphasized basis image $BG1a$, a heat map $61a$ is added to the portion corresponding to the solidity serving as a basis of the change in the property item. Further, in the emphasized basis image $BG2a$, a heat map $61b$ is added to the portion corresponding to the property in which the change has occurred, that is, the boundary of the tumor. In FIG. 22, the heat maps $61a$ and $61b$ are shown by diagonal lines for the sake of simplification.

In the third embodiment, the display control unit 24 displays the emphasized basis images $BG1a$ and $BG2a$ for the first and second medical images G1 and G2 on the display 14. Specifically, as in the first embodiment, the report creation screen is displayed on the display 14, and the emphasized basis image is displayed according to the instruction of the operator using the report creation screen.

Figure 23:
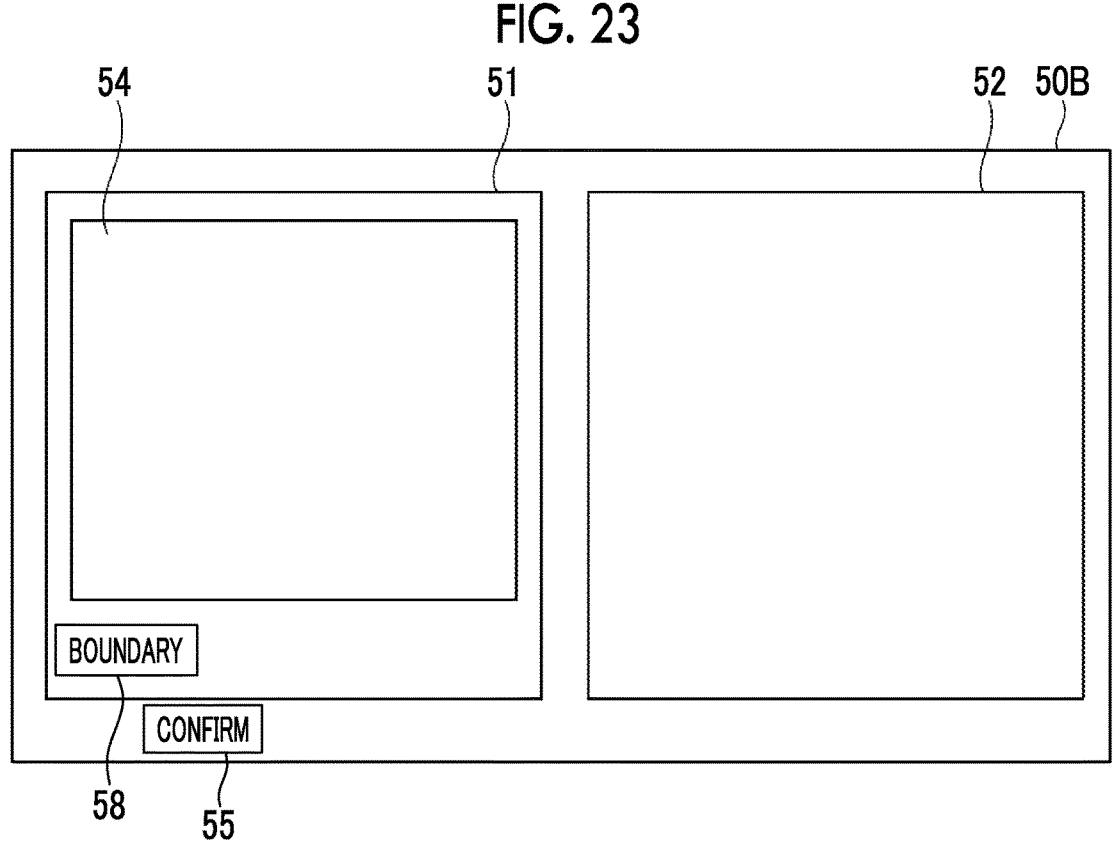
FIG. 23 is a diagram showing a report creation screen in the third embodiment.

FIG. 23 is a diagram showing a report creation screen in the third embodiment. As shown in FIG. 23, a report creation screen 50B includes the sentence display region 51 and the image display region 52, similarly to the report creation screen 50 in the first embodiment. In the sentence display region 51, a designation button 58 and the findings input region 54 are included. A character of the boundary, which is a property in which changes in the first and second medical images G1 and G2 have occurred, is added to the designation button 58.

Figure 24:
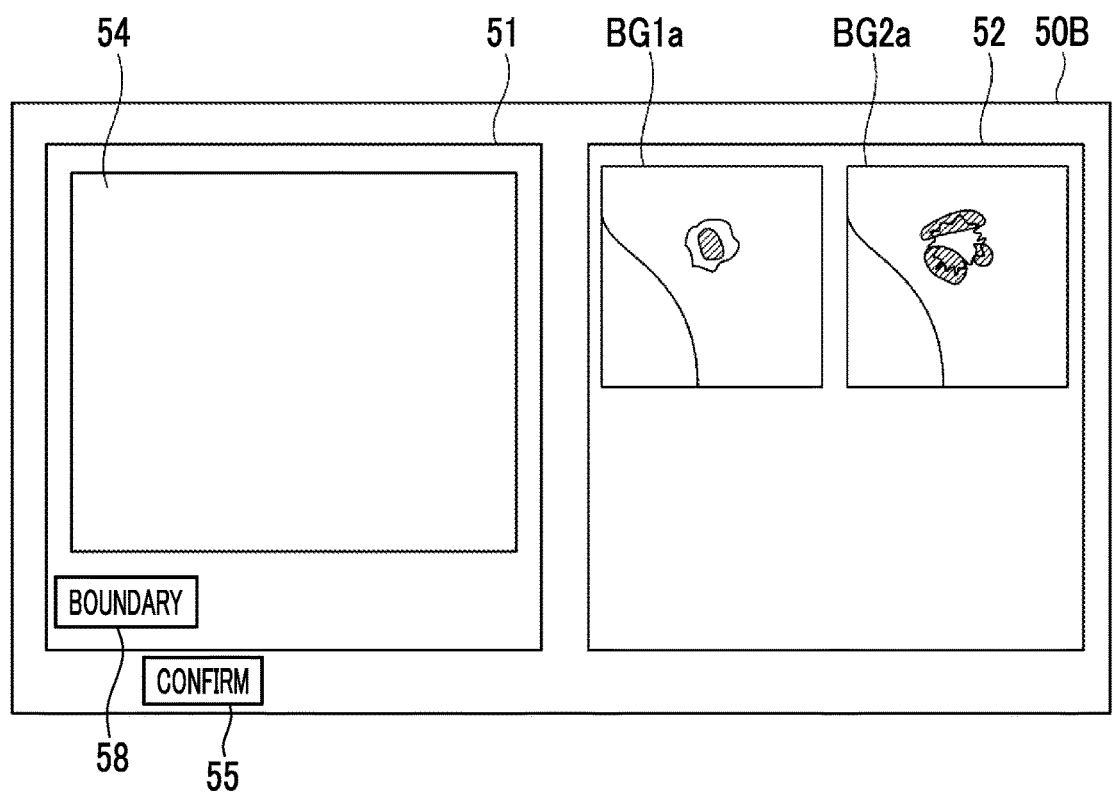
FIG. 24 is a diagram showing the report creation screen in the third embodiment.

Then, in a case where the operator selects the designation button 58 on the report creation screen 50B, the display control unit 24 displays the emphasized basis images $BG1a$ and $BG2a$ for the two medical images G1 and G2 in the image display region 52. FIG. 24 is a diagram showing the report creation screen in which the emphasized basis images are displayed in the third embodiment. As shown in FIG. 24, two emphasized basis images $BG1a$ and $BG2a$ are displayed in the image display region 52 of the report creation screen 50B. The operator can easily check the property in which the change has occurred in the displayed two emphasized basis images $BG1a$ and $BG2a$.

In the third embodiment, creation, saving, and transmission of the interpretation report are the same as those in the first embodiment, and therefore, detailed description thereof will be omitted here.

Further, in the third embodiment, as in the second embodiment, the phrase related to the property item included in the comments on findings may be specified, and information for accessing the basis image serving as a basis for deriving the properties represented by the specified phrase may be added thereto.

In addition, in each of the above embodiments, an interpretation report including the comments on findings input by the operator is created, but the present disclosure is not limited thereto. The report creation unit 25 may automatically generate comments on findings based on the property item derived by the property derivation unit 22. In this case, the report creation unit 25 has a learning model that has been trained to output a sentence including the property information in a case where the property information is input. As the learning model, for example, a recurrent neural network can be used.

Further, in each of the above embodiments, the basis image and the heat map for the basis image are combined to derive the emphasized basis image in which the basis region is emphasized, but the present disclosure is not limited thereto. Instead of creating a heat map, the emphasized basis image may be derived by adding a mark such as an arrow to the basis region in the basis image as an annotation or adding text information such as a comment together.

Further, in each of the above embodiments, although the interpretation report creation support process is performed using a medical image with the lung as the diagnosis target, the diagnosis target is not limited to the lung. In addition to the lung, any part of a human body such as a heart, liver, brain, and limbs can be diagnosed.

In the interpretation report, the diagnosis result of the radiologist may be described as diagnostic information based on at least one piece of property information. In the present embodiment, information for accessing at least one piece of property information from the diagnostic information may be added to the diagnostic information described in the interpretation report. In a case where there are a plurality of pieces of property information, information for accessing each piece of the property information from the diagnostic information may be added. Further, in the present embodiment, since the basis image is associated with each property item for which the property information is specified, the basis image may be accessed at the same time in the case where the property information is accessed from the diagnostic information.

Further, in each of the above embodiments, for example, as hardware structures of processing units that execute various kinds of processing, such as the image acquisition unit 21, the property derivation unit 22, the basis image derivation unit 23, the display control unit 24, the report creation unit 25, the communication unit 26, and the phrase specifying unit 27, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor. As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by using one or more of the above-described various processors as hardware structures.

Furthermore, as the hardware structure of the various processors, more specifically, an electrical circuit (circuitry) in which circuit elements such as semiconductor elements are combined can be used.

What is claimed is:

1. An information processing apparatus comprising at least one processor, wherein the processor is configured to
   receive a plurality of medical images;
   input the plurality of medical images into a trained model;
   derive, from the trained model, property information indicating a property for at least one predetermined property item which is related to a structure of interest included in each of the plurality of medical images;
   select, from the plurality of medical images, a basis image which has a most prominent property information of the property of the at least one predetermined property item among the plurality of medical images, wherein the most prominent property information represents a size of a basis region being the largest; and
   specify, in the basis image, the basis region serving as a basis for deriving the property related to the structure of interest.

2. The information processing apparatus according to claim 1, wherein the basis image includes a plurality of basis images, and the processor is further configured to
   combine the basis images and images of the plurality of medical images that corresponds to the basis images to derive a first emphasize image in which the basis region is emphasized.

3. The information processing apparatus according to claim 1, wherein the processor is configured to
   display, in an area of a user interface, the basis image;
   select, from the user interface, a first area corresponding the first property item;
   display the first emphasized basis image corresponding the first property item in response to selecting the first area;
   select, from the user interface, a second area corresponding the second property item; and
   display a second emphasized basis image corresponding the second property item in response to selecting the second area.

4. The information processing apparatus according to claim 1, wherein the processor is configured to
   derive the property for the property item in which a change has occurred with respect to the structure of interest between a first image acquired at a first point in time and a second image acquired at a second point in time different from the first point in time, and
   for the property item in which the change has occurred in the property between the first image and the second image, specify the basis region in at least one of the first image or the second image and derive the basis image.

5. The information processing apparatus according to claim 1, wherein the processor is configured to
display a designation button for designating at least one property item on a display, and
select the designation button to display a basis image for a property item corresponding to the selected designation button on the display.

6. The information processing apparatus according to claim 5, wherein the processor is configured to highlight the basis region in the displayed basis image.

7. The information processing apparatus according to claim 1, wherein the processor is configured to
analyze a sentence including phrases related to the property item to specify a phrase related to the property item included in the sentence and add, to the specified phrase, information for accessing the basis image serving as a basis for deriving the property represented by the specified phrase, and
display the sentence on a display and display the basis image corresponding to the phrase selected in the sentence on the display.

8. The information processing apparatus according to claim 7, wherein the processor is configured to generate the sentence by using the property for the property item.

9. An information processing method executed by a processor of an information processing apparatus, the method comprising:
receiving a plurality of medical images;
inputting the plurality of medical images into a trained model;
deriving, from the trained model, property information indicating a property for at least one predetermined property item which is related to a structure of interest included in each of the plurality of medical images;
selecting, from the plurality of medical images, a basis image which has a most prominent property information of the property of the at least one predetermined property item among the plurality of medical images, wherein the most prominent property information represents a size of a basis region being the largest; and
specifying, in the basis image, the basis region serving as a basis for deriving the property related to the structure of interest.

10. A non-transitory computer-readable storage medium that stores an information processing program for causing a a processor of an information processing apparatus to execute a procedure comprising:
receiving a plurality of medical images;
inputting the plurality of medical images into a trained model;
deriving, from the trained model, property information indicating a property for at least one predetermined property item which is related to a structure of interest included in each of the plurality of medical images;
selecting, from the plurality of medical images, a basis image which has a most prominent property information of the property of the at least one predetermined property item among the plurality of medical images, wherein the most prominent property information represents a size of a basis region being the largest; and
specifying, in the basis image, the basis region serving as a basis for deriving the property related to the structure of interest.

* * * * *